(12) United States Patent
Cirillo et al.

(10) Patent No.: US 7,279,475 B2
(45) Date of Patent: Oct. 9, 2007

(54) FLUORINATED DI-ARYL UREA COMPOUNDS

(75) Inventors: Pier Francesco Cirillo, Woodbury, CT (US); Abdelhakim Hammach, Danbury, CT (US); Victor Kamhi, Danbury, CT (US); Neil Moss, Ridgefield, CT (US); Paul S Riska, Danbury, CT (US); Christopher Pargellis, Redding, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 512 days.

(21) Appl. No.: 10/940,898

(22) Filed: Sep. 14, 2004

(65) Prior Publication Data

US 2005/0032797 A1 Feb. 10, 2005

Related U.S. Application Data

(62) Division of application No. 10/632,998, filed on Aug. 1, 2003, now Pat. No. 6,872,726.

(60) Provisional application No. 60/401,921, filed on Aug. 8, 2002.

(51) Int. Cl.
  *A61K 31/5377* (2006.01)
  *A61K 31/496* (2006.01)
  *C07D 413/06* (2006.01)
  *C07D 403/06* (2006.01)

(52) U.S. Cl. .................. 514/235.8; 544/106; 544/111; 544/114; 544/122; 544/224; 544/336; 544/356; 544/359; 544/123; 514/231.2; 514/231.5; 514/235.5; 514/247; 514/252.1; 514/252.12; 514/252.13

(58) Field of Classification Search ................ 544/106, 544/111, 114, 122, 123, 224, 336, 356, 359; 514/231.2, 235.5, 247, 252.12, 252.13, 235.8
See application file for complete search history.

(56) References Cited

U.S. PATENT DOCUMENTS 6,080,763 A  6/2000 Regan et al.
6,287,381 B1  9/2001 Klocek
6,319,721 B1  11/2001 Kosaka
6,329,415 B1  12/2001 Cirillo et al.
6,358,945 B1  3/2002 Breitfelder et al.
6,492,393 B1 *  12/2002 Breitfelder et al. ......... 514/319
6,872,726 B2 *  3/2005 Cirillo et al. ............... 514/256
2002/0065296 A1  5/2002 Dumas et al.

FOREIGN PATENT DOCUMENTS

| WO | WO99/32110 | 7/1999 |
|---|---|---|
| WO | WO99/32463 A1 | 7/1999 |
| WO | WO 00/41698 A1 | 7/2000 |
| WO | WO 01/36403 A1 | 5/2001 |
| WO | WO 02/083628 A1 | 10/2002 |
| WO | WO 02/092576 A1 | 11/2002 |

* cited by examiner

*Primary Examiner*—Golam M. M. Shameem
(74) *Attorney, Agent, or Firm*—Michael Morris; Mary-Ellen M. Devlin; Anthony P. Bottino

(57) ABSTRACT

Disclosed are compounds of formula(I):

(I)

wherein $R_1$, $R_2$, W and X of formula(I) are defined herein. The compounds inhibit production of cytokines involved in inflammatory processes and are thus useful for treating diseases and pathological conditions involving inflammation such as chronic inflammatory disease. Also disclosed are processes for preparing these compounds and pharmaceutical compositions comprising these compounds.

10 Claims, No Drawings

FLUORINATED DI-ARYL UREA COMPOUNDS

RELATED APPLICATION DATA

This application is a divisional application of U.S. application Ser. No. 10/632,998 filed Aug. 1, 2003 which claims benefit to U.S. provisional application No. 60/401,921 filed Aug. 8, 2002.

TECHNICAL FIELD OF THE INVENTION

This invention relates to fluorinated di-aryl urea compounds compounds of formula(I):

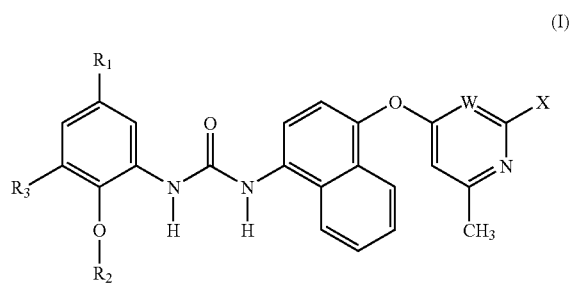

wherein $R_1$, $R_2$, $R_3$, X and W of formula(I) are defined below. The compounds of the invention inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

BACKGROUND OF THE INVENTION

Compounds useful as p38 MAP kinase inhibitors are known and have been shown to be useful for inhibiting cytokine production. Pargellis C., et al. 2002, Nat Struct Biol. 9:268-272.

Tumor necrosis factor (TNF) and interleukin-1 (IL-1) are important biological entities collectively referred to as proinflammatory cytokines which play a role in cytokine mediated diseases. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, *Rev. Infect. Disease* 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J. Invest. Med.* 43: 28-38). Studies suggest that inflammatory changes mediated by cytokines may be involved in endothelial cell pathogenesis including restenosis after percutaneous transluminal coronary angioplasty (PTCA) (Tashiro, H., et al., 2001 Mar, *Coron Artery Dis* 12(2):107-13). An important and accepted therapeutic approach for potential drug intervention in these diseases is the reduction of proinflammatory cytokines such as TNF (also referred to in its secreted cell-free form as TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24-5, 1997). These include the treatment of rheumatoid arthritis, Crohn's disease and ulcerative colitis (Rankin, E. C. C., et al., 1997, *British J Rheum.* 35: 334-342 and Stack, W. A., et al., 1997, *Lancet* 349: 521-524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, *Nature Biotechnology* 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, *Inflamm. Res.* 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrition* 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, *Biomed Pharmacother.* 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner Res.* 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, *Proc Soc Exp Biol Med.* 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A,* 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, *Med Hypotheses,* 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol.* 109, 54). IL-1 and TNF are both involved in periodontal disease. The destructive process associated with periodontal disease may be due to a disregulation of both IL-1 and TNF (Howells, 1995, *Oral Dis.* 1, 266).

Proinflammatory cytokines such as TNFα and IL-1β are also important mediators of septic shock and associated cardiopulmonary dysfunction, acute respiratory distress syndrome (ARDS) and multiple organ failure. In a study of patients presenting at a hospital with sepsis, a correlation was found between TNFα and IL-6 levels and septic complications (Terregino et al., 2000, *Ann. Emerg. Med.,* 35, 26). TNFα has also been implicated in cachexia and muscle degradation, associated with HIV infection (Lahdiverta et al., 1988, *Amer. J. Med.,* 85, 289). Obesity is associated with an increase incidence of infection, diabetes and cardiovascular disease. Abnormalities in TNFα expression have been noted for each of the above conditions (Loffreda, et al., 1998, *FASEB J.* 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol.* 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation,* 97, 242).

TNFα levels are elevated in airways of patients with chronic obstructive pulmonary disease and it may contribute to the pathogenesis of this disease (M. A. Higham et al., 2000, *Eur. Respiratory J.,* 15, 281). Circulating TNFα may also contribute to weight loss associated with this disease (N. Takabatake et al., 2000, *Amer. J. Resp. & Crit. Care Med.,* 161 (4 Pt 1), 1179). Elevated TNFα levels have also been found to be associated with congestive heart failure and the level has been correlated with severity of the disease (A. M. Feldman et al., 2000, *J. Amer. College of Cardiology,* 35, 537). In addition, TNFα has been implicated in reperfusion injury in lung (Borjesson et al., 2000, *Amer. J. Physiol.,* 278, L3-12), kidney (Lemay et al., 2000, *Transplantation,* 69, 959), and the nervous system (Mitsui et al., 1999, *Brain Res.,* 844, 192).

TNFα is also a potent osteoclastogenic agent and is involved in bone resorption and diseases involving bone resorption (Abu-Amer et al., 2000, *J. Biol. Chem.,* 275, 27307). It has also been found highly expressed in chondrocytes of patients with traumatic arthritis (Melchiorri et al., 2000, *Arthritis and Rheumatism,* 41, 2165). TNFα has also been shown to play a key role in the development of glomerulonephritis (Le Hir et al., 1998, *Laboratory Investigation,* 78, 1625).

The abnormal expression of inducible nitric oxide synthetase (iNOS) has been associated with hypertension in the spontaneously hypertensive rat (Chou et al., 1998, *Hypertension,* 31, 643). IL-1 has a role in the expression of iNOS and therefore may also have a role in the pathogenesis of hypertension (Singh et al., 1996, *Amer. J. Hypertension,* 9, 867).

IL-1 has also been shown to induce uveitis in rats which could be inhibited with IL-1 blockers. (Xuan et al., 1998, *J. Ocular Pharmacol. and Ther.,* 14, 31). Cytokines including IL-1, TNF and GM-CSF have been shown to stimulate proliferation of acute myelogenous leukemia blasts (Bruserud, 1996, *Leukemia Res.* 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, *Am J Contact Dermat.* 7, 177). Data obtained from IL-1 knock out mice indicates the critical involvement in fever for this cytokine (Kluger et al., 1998, *Clin Exp Pharmacol Physiol.* 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr.* 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopheresis, granulocyte transfusion associated syndromes, and necrotizing enterocolitis.

Rhinovirus triggers the production of various proinflammatory cytokines, predominantly IL-8, which results in symptomatic illnesses such as acute rhinitis (Winther et al., 1998, *Am J Rhinol.* 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21: 487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokins Mol Ther.* 1, 107). Several infectious diseases, such as influenza, indicate IL-6 and IFN alpha as key factors in both symptom formation and in host defense (Hayden, et al., 1998, *J Clin Invest.* 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J. Med. Chem.,* 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56).

Interferon γ (IFN γ) has been implicated in a number of diseases. It has been associated with increased collagen deposition that is a central histopathological feature of graft-versus-host disease (Parkman, 1998, *Curr Opin Hematol.* 5, 22). Following kidney transplantation, a patient was diagnosed with acute myelogenous leukemia. Retrospective analysis of peripheral blood cytokines revealed elevated levels of GM-CSF and IFN γ. These elevated levels coincided with a rise in peripheral blood white cell count (Burke, et al., 1995, *Leuk Lymphoma.* 19, 173). The development of insulin-dependent diabetes (Type 1) can be correlated with the accumulation in pancreatic islet cells of T-cells producing IFN γ (Ablumunits, et al., 1998, *J Autoimmun.* 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce MRNA specific for IFN γ following challenge with Vespula venom (Bonay, et al., 1997, *Clin Exp Immunol.* 109, 342). The expression of a number of cytokines, including IFN γ has been shown to increase following a delayed type hypersensitivity reaction thus indicating a role for IFN γ in atopic dermatitis (Szepietowski, et al., 1997, *Br J Dermatol.* 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am J Trop Med Hyg.* 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al., 1998, *Proc Soc Exp Biol Med.* 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ, TNF and IL-2 (Chisari, et al., 1995, *Springer Semin Immunopathol.* 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: rheumatoid arthritis, tumor associated osteolysis and post-menopausal osteoporosis (Evans, et al., 1996, *J Bone Miner Res.* 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon.* 43, 277). IFN γ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther.* 10 *Suppl* 2, 43). An elevated level of serum IgE is associated with various atopic diseases such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

WO 01/01986 discloses particular compounds alleged to having the ability to inhibit TNF-alpha. Certain compounds disclosed in WO 01/01986 are indicated to be effective in treating the following diseases: dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalophathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia. WO 02/32862 discloses that inhibitors of pro-inflammatory cytokines including TNFα are allegedly useful for treating acute and chronic inflammation in the lung caused by inhalation of smoke such as cigarette smoke. TNFα anatagonists are apparently also useful for the treatment of endometriosis, see EP 1022027 A1. Infliximab, in clinical trials for RA, has also been indicated to be useful for treating various inflammatory diseases including Behcet's disease, uveitis and ankylosing spondylitis. Pancreatitis may also be regulated by inflammatory mediator production, see J Surg Res 2000 May 15 90(2)95-101; Shock 1998 Sep. 10(3):160-75. p38MAPkinase pathway plays an role in B.burgdorferi-elicited infammation and may be useful in treating inflammation induced by the Lyme disease agent. Anguita, J. et. al., *The Journal of Immunology,* 2002, 168:6352-6357.

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas and their use in treating cytokine diseases and proteolytic enzyme mediated disease. WO 00/41698 discloses aryl ureas said to be useful in treating p38 MAP kinase diseases.

U.S. Pat. No. 5,162,360 discloses N-substituted aryl-N'-heterocyclic substituted urea compounds which are described as being useful for treating hypercholesterolemia and atheroclerosis. Di-substituted aryl and heteroaryl compounds are also disclosed in U.S. Pat. Nos. 6,080,763; 6,319,921; 6,297,381 and 6,358,945. The compounds in the patents are alleged to possess anti-cytokine activity and are therefore useful in treating diseases associated with inflammation.

WO 01/36403 discloses heteroaryl urea compounds useful for treating cytokine mediated diseases. Certain example compounds possess flourinated alkyl and cycloalkyl substituted phenyl moities at the 3-urea position, and other distinct compounds possess substituted pyrimidinyloxynaphthyl moities at the 1-urea position. The compounds in the present application disclosed herein below differ structurally and by possessing a better combination of desirable properties: phamacokinetics, potency and selectivity for p38 MAP kinase.

The work cited above supports the principle that inhibition of cytokine production will be beneficial in the treatment of cytokine mediated diseases. Therefore a need exists for small molecule inhibitors for treating these diseases with optimized efficacy, pharmacokinetic and safety profiles.

BRIEF SUMMARY OF THE INVENTION

The work cited above supports the principle that inhibition of cytokine production with compounds possessing an improved combination of pharmacokinetics, potency and selectivity for p38 MAP kinase will be beneficial in the treatment of various disease states.

It is therefore an object of the invention to provide flourinated di-aryl urea compounds of formula(I):

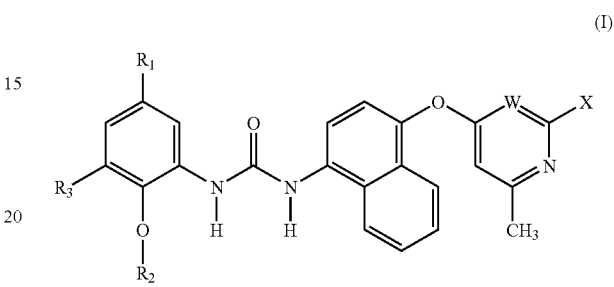

wherein $R_1$, $R_2$, $R_3$, W and X of formula(I) are defined below

It is a further object of the invention to provide methods for treating cytokine mediated diseases and pathological conditions involving inflammation such as chronic inflammatory disease, using the novel compounds of the invention.

It is yet a further object of the invention to provide processes of preparation of the above-mentioned novel compounds.

DETAILED DESCRIPTION OF THE INVENTION

In a generic aspect of the invention, there are provided compounds of the formula (I):

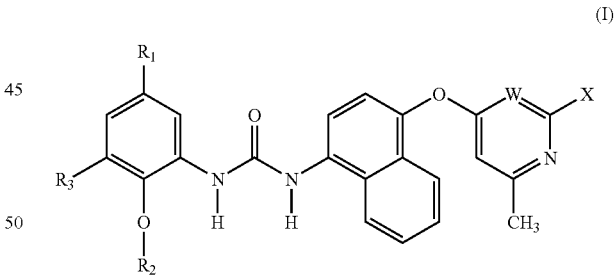

wherein
$R_1$ is —$CF_3$, —$CH(CH_3)(CF_3)$, —$CH(CF_3)_2$, —$OCF_3$, —$CF_2CF_3$;
$R_2$ is $C_{1-5}$ alkyl;
$R_3$ is attached at the 3- or 4-position on the phenyl ring and is hydrogen, —$NH_2$ or $R_4$—$S(O)_2$—NH— wherein $R_4$ is chosen from $C_{1-5}$ alkyl or carbocycle;
W is CH or an N atom;
X is chosen from
C1-5 alkyl or C1-5 alkoxy each optionally substituted by mono- or di-C1-3 alkyl amino, morpholinyl, piperazinyl, pyrrolidinyl, triazolyl, imidazolyl or piperadinyl each ring being further optionally substituted with C1-3 alkyl;

or X is —N(R$^a$)$_2$ wherein R$^a$ is independently chosen from hydrogen, C1-5 alkyl, aryl, arylC1-3 alkyl, C3-7cycloalkyl, C3-7cycloalkyl C1-3 alkyl, C1-5alkoxyC1-5alkyl and heterocyclyl C1-3 alkyl wherein the heterocycyl is chosen from tetrahydrofuran, pyrrolidinyl and morpholinyl, each R$^a$ where possible is optionally substituted by one to two C1-5 alkyl, C1-5 alkoxy, hydroxy, halogen or amino optionally mono- or di-substituted by C1-3 alkyl;

or the pharmaceutically acceptable acids, esters, salts or isomers thereof.

In another embodiment there is provided compounds of the formula (I) as described immediately above and wherein:

R$_1$ is —CF$_3$, —CH(CH$_3$)(CF$_3$), —CH(CF$_3$)$_2$, —OCF$_3$ or —CF$_2$CF$_3$;

R$_2$ is C$_{1-3}$ alkyl;

W is an N atom;

X is chosen from

C1-5 alkyl or C1-5 alkoxy each optionally substituted by mono- or di-C1-3 alkyl amino, morpholinyl, piperazinyl, pyrrolidinyl, triazolyl, imidazolyl or piperadinyl each ring being further optionally substituted with C1-3 alkyl;

or X is —N(R$^a$)$_2$ wherein R$^a$ is independently chosen from hydrogen, C1-5 alkyl, phenylC1-3 alkyl, C3-6cycloalkyl, C3-6cycloalkyl C1-3 alkyl, C1-3alkoxyC1-3alkyl and heterocyclyl C1-3 alkyl wherein the heterocycyl is chosen from tetrahydrofuran, pyrrolidinyl and morpholinyl, each R$^a$ where possible is optionally substituted by one to two C1-3 alkyl, C1-3 alkoxy, hydroxy, halogen or amino optionally mono- or di-substituted by C1-2 alkyl.

In yet another embodiment there is provided compounds of the formula (I) as described immediately above and wherein:

R$_1$ is —CF$_3$, —CH(CH$_3$)(CF$_3$), —CH(CF$_3$)$_2$ or —CF$_2$CF$_3$;

R$_2$ is C$_{1-2}$ alkyl.

In yet still another embodiment there is provided compounds of the formula (I) as described immediately above and wherein:

R$_1$ is —CF$_3$;

R$_2$ is —CH$_3$.

In yet still another embodiment there is provided compounds of the formula (I) as described immediately above and wherein:

X is chosen from

NH$_2$, NH(CH$_3$), —NHCH$_2$CH$_2$N(CH$_3$)$_2$, —NHCH$_2$CH$_2$—O—CH$_3$, —CH$_2$—N(CH$_3$)$_2$, —CH$_2$CH$_2$—N(CH$_3$)$_2$, —CH$_2$CH$_2$CH$_2$—N(CH$_3$)$_2$, —CH$_2$CH$_2$CH$_2$CH$_2$—N(CH$_3$), —CH$_2$CH$_2$—NH(CH$_3$), —CH$_2$CH$_2$CH$_2$—NH(CH$_3$), —CH$_2$CH$_2$CH$_2$CH$_2$—NH(CH$_3$), —O—CH$_2$—N(CH$_3$)$_2$, —O—CH$_2$CH$_2$—N(CH$_3$)$_2$, —O—CH$_2$CH$_2$CH$_2$—N(CH$_3$)$_2$, —O—CH$_2$CH$_2$CH$_2$CH$_2$—N(CH$_3$)$_2$, —OCH$_2$—NH(CH$_3$), —O—CH$_2$CH$_2$—NH(CH$_3$), —O—CH$_2$CH$_2$CH$_2$—NH(CH$_3$), —O—CH$_2$CH$_2$CH$_2$CH$_2$—NH(CH$_3$),

—CH$_2$CH$_2$—N(piperazinyl-N—CH$_3$),

-continued

—CH$_2$CH$_2$—N(piperidinyl),

—CH$_2$CH$_2$—N(morpholinyl), —CH$_2$—N(morpholinyl),

—NHCH$_2$—(tetrahydrofuranyl), —NHCH$_2$CH$_2$—N(pyrrolidinyl),

—CH$_2$CH$_2$—N(pyrrolidinyl) and —NHCH$_2$CH$_2$—N(morpholinyl).

In yet still another embodiment there is provided compounds of the formula (I) as described immediately above and wherein:

X is chosen from

NH$_2$, NH(CH$_3$), —NHCH$_2$CH$_2$N(CH$_3$)$_2$, —NHCH$_2$CH$_2$—O—CH$_3$, —CH$_2$—N(CH$_3$)$_2$, —CH$_2$CH$_2$—N(CH$_3$)$_2$, —CH$_2$CH$_2$CH$_2$—N(CH$_3$)$_2$, —CH$_2$—NH(CH$_3$), —CH$_2$CH$_2$—NH(CH$_3$), —CH$_2$CH$_2$CH$_2$—NH(CH$_3$), —CH$_2$CH$_2$CH$_2$CH$_2$—NH(CH$_3$), —O—CH$_2$—N(CH$_3$)$_2$, —O—CH$_2$CH$_2$—N(CH$_3$)$_2$, —O—CH$_2$CH$_2$CH$_2$—N(CH$_3$), —O—CH$_2$CH$_2$CH$_2$CH$_2$—N(CH$_3$)$_2$, —OCH$_2$—NH(CH$_3$), —O—CH$_2$CH$_2$—NH(CH$_3$), —O—CH$_2$CH$_2$CH$_2$—NH(CH$_3$), —O—CH$_2$CH$_2$CH$_2$CH$_2$—NH(CH$_3$),

—CH$_2$—N(morpholinyl), —NHCH$_2$—(tetrahydrofuranyl),

—NHCH$_2$CH$_2$—N(pyrrolidinyl) and

—NHCH$_2$CH$_2$—N(morpholinyl).

The following are representative compounds of the invention:

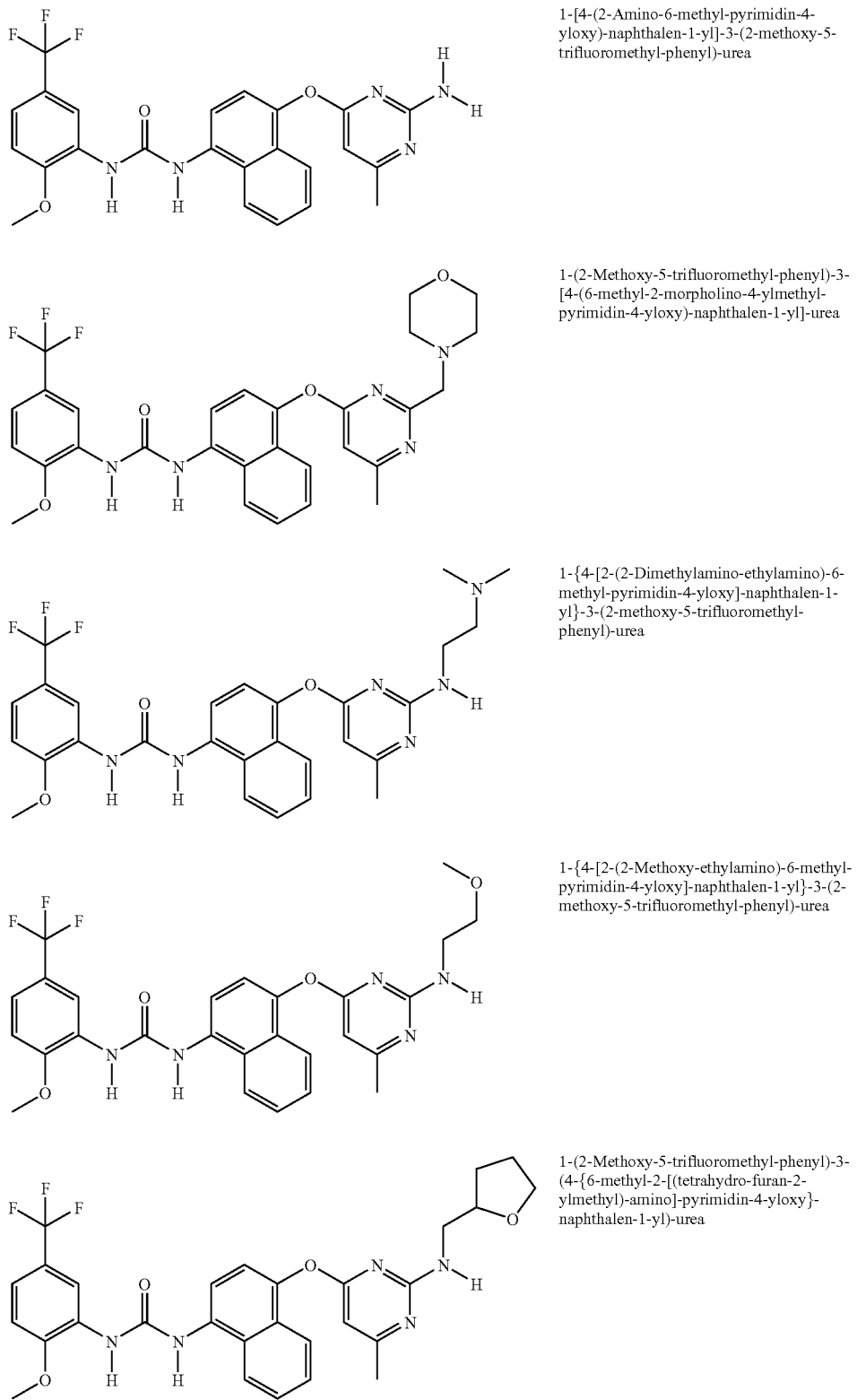

1-[4-(2-Amino-6-methyl-pyrimidin-4-yloxy)-naphthalen-1-yl]-3-(2-methoxy-5-trifluoromethyl-phenyl)-urea 1-(2-Methoxy-5-trifluoromethyl-phenyl)-3-[4-(6-methyl-2-morpholino-4-ylmethyl-pyrimidin-4-yloxy)-naphthalen-1-yl]-urea 1-{4-[2-(2-Dimethylamino-ethylamino)-6-methyl-pyrimidin-4-yloxy]-naphthalen-1-yl}-3-(2-methoxy-5-trifluoromethyl-phenyl)-urea 1-{4-[2-(2-Methoxy-ethylamino)-6-methyl-pyrimidin-4-yloxy]-naphthalen-1-yl}-3-(2-methoxy-5-trifluoromethyl-phenyl)-urea 1-(2-Methoxy-5-trifluoromethyl-phenyl)-3-(4-{6-methyl-2-[(tetrahydro-furan-2-ylmethyl)-amino]-pyrimidin-4-yloxy}-naphthalen-1-yl)-urea

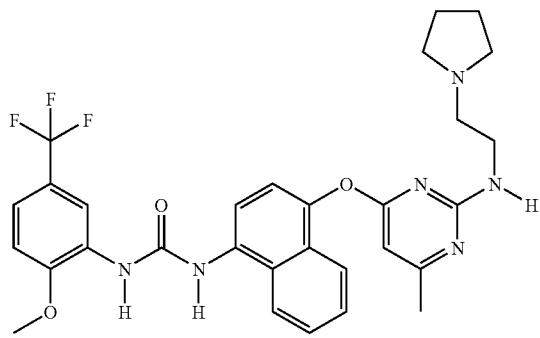

1-(2-Methoxy-5-trifluoromethyl-phenyl)-3-{4-[6-methyl-2-(2-pyrrolidin-1-yl-ethylamino)-pyrimidin-4-yloxy]-naphthalen-1-yl}-urea

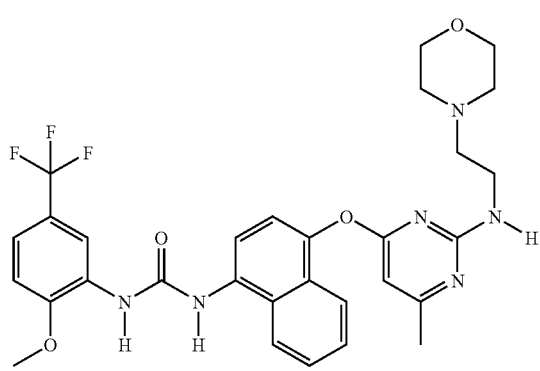

1-(2-Methoxy-5-trifluoromethyl-phenyl)-3-{4-[6-methyl-2-(2-morpholino-4-yl-ethylamino)-pyrimidin-4-yloxy]-naphthalen-1-yl}-urea

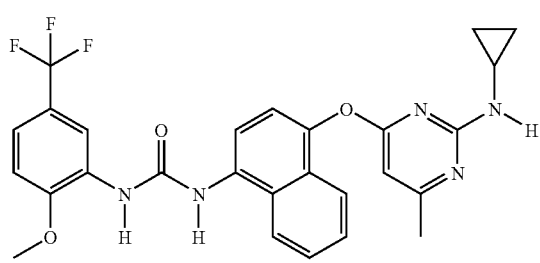

1-[4-(2-Cyclopropylamino-6-methyl-pyrimidin-4-yloxy)-naphthalen-1-yl]-3-(2-methoxy-5-trifluoromethyl-phenyl)-urea

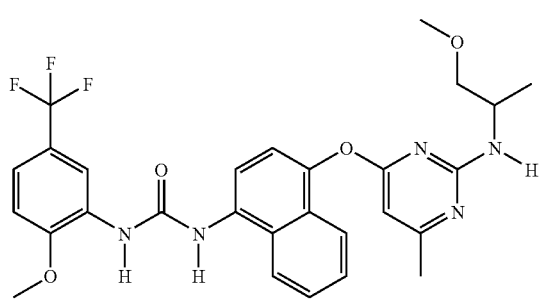

1-{4-[2-(2-Methoxy-1-methyl-ethylamino)-6-methyl-pyrimidin-4-yloxy]-naphthalen 1-yl}-3-(2-methoxy-5-trifluoromethyl-phenyl)-urea

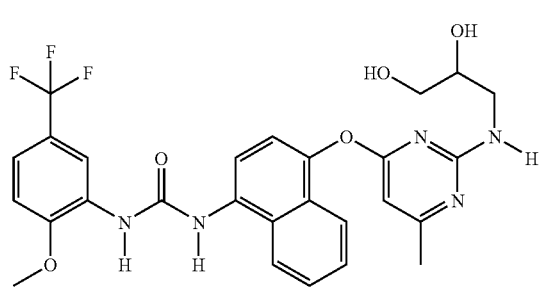

1-{4-[2-(2,3-Dihydroxy-propylamino)-6-methyl-pyrimidin-4-yloxy]-naphthalen-1-yl}-3-(2-methoxy-5-trifluoromethyl-phenyl)-urea -continued

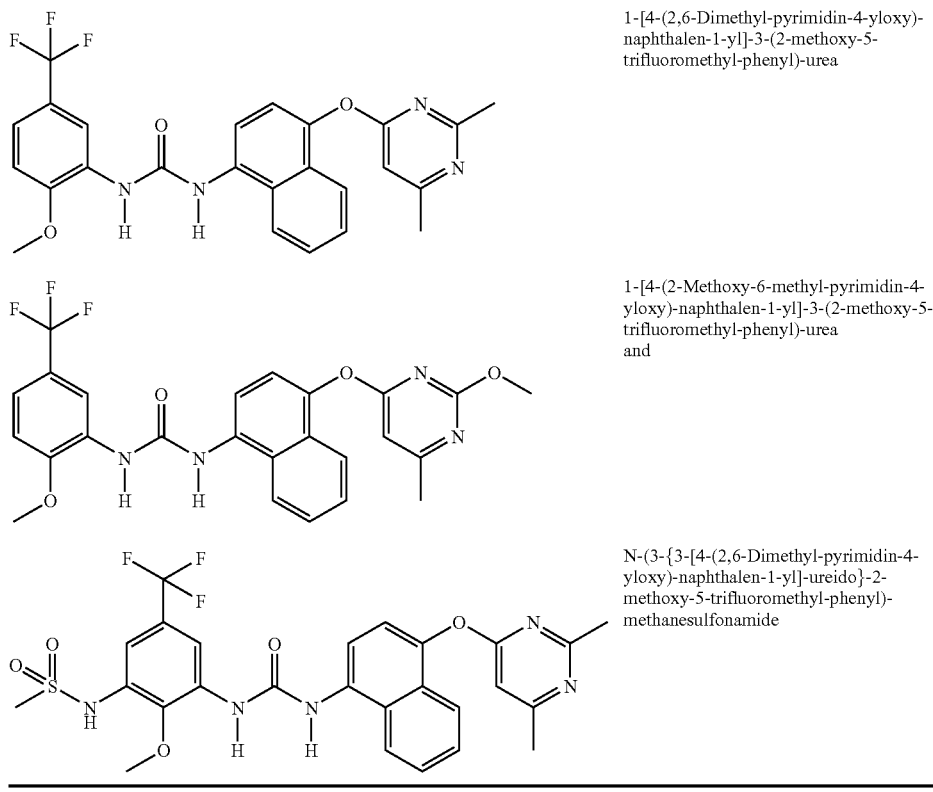

1-[4-(2,6-Dimethyl-pyrimidin-4-yloxy)-naphthalen-1-yl]-3-(2-methoxy-5-trifluoromethyl-phenyl)-urea 1-[4-(2-Methoxy-6-methyl-pyrimidin-4-yloxy)-naphthalen-1-yl]-3-(2-methoxy-5-trifluoromethyl-phenyl)-urea
and N-(3-{3-[4-(2,6-Dimethyl-pyrimidin-4-yloxy)-naphthalen-1-yl]-ureido}-2-methoxy-5-trifluoromethyl-phenyl)-methanesulfonamide or the pharmaceutically acceptable acids, esters, salts or isomers thereof.

The following are compounds of the invention which may be made by the general synthetic schemes and working examples:

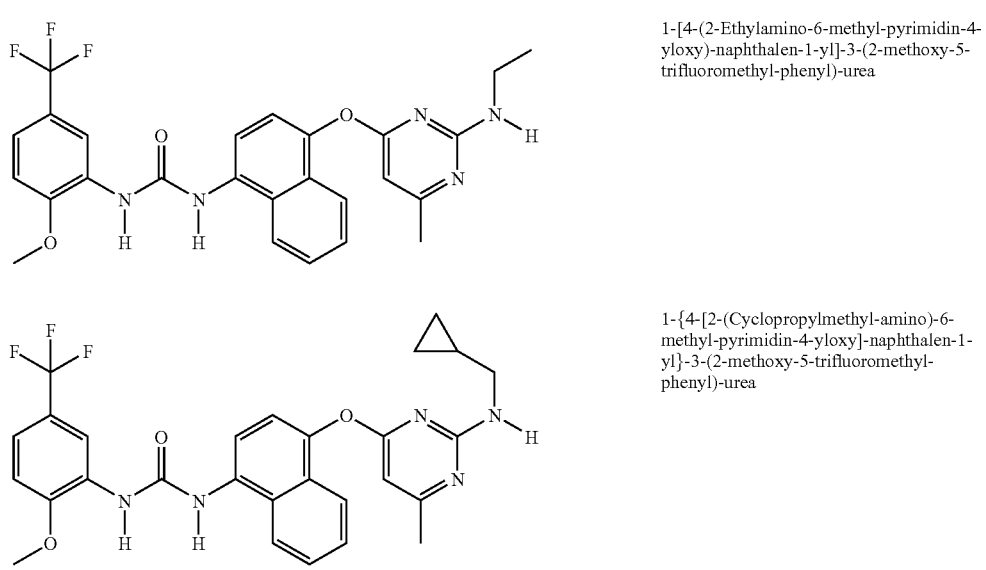

1-[4-(2-Ethylamino-6-methyl-pyrimidin-4-yloxy)-naphthalen-1-yl]-3-(2-methoxy-5-trifluoromethyl-phenyl)-urea 1-{4-[2-(Cyclopropylmethyl-amino)-6-methyl-pyrimidin-4-yloxy]-naphthalen-1-yl}-3-(2-methoxy-5-trifluoromethyl-phenyl)-urea

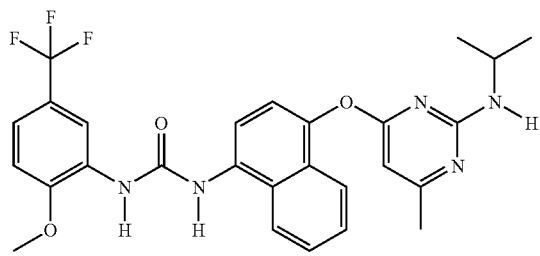

1-[4-(2-Isopropylamino-6-methyl-pyrimidin-4-yloxy)-naphthalen-4-yl]-3-(2-methoxy-5-trifluoromethyl-phenyl)-urea

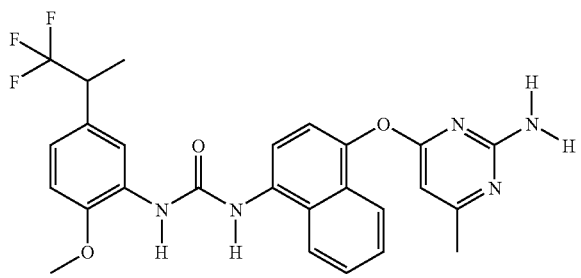

1-[4-(2-Amino-6-methyl-pyrimidin-4-yloxy)-naphthalen-1-yl]-3-[2-methoxy-5-(2,2,2-trifluoro-1-methyl-ethyl)-phenyl]-urea

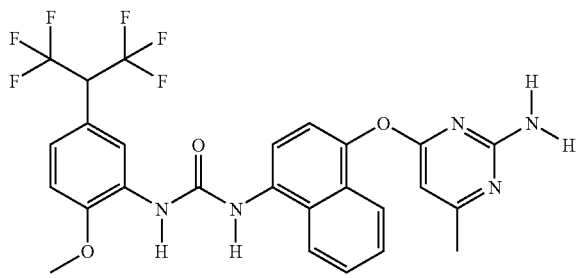

1-[4-(2-Amino-6-methyl-pyrimidin-4-yloxy)-naphthalen-1-yl]-3-[2-methoxy-5-(2,2,2-trifluoro-1-trifluoromethyl-ethyl)-phenyl]-urea

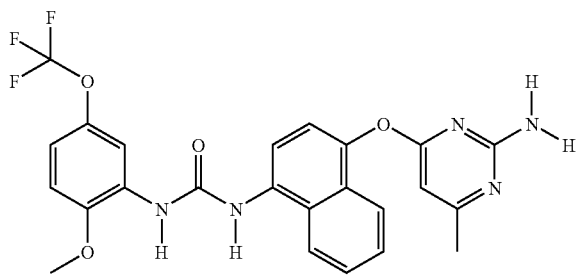

1-[4-(2-Amino-6-methyl-pyrimidin-4-yloxy)-naphthalen-1-yl]-3-[2-methoxy-5-(2,2,2-trifluoro-ethyl)-phenyl]-urea

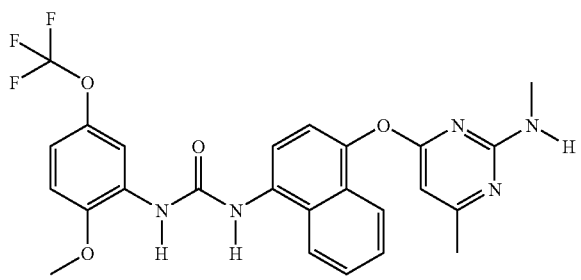

1-[4-(2-Methylamino-6-methyl-pyrimidin-4-yloxy)-naphthalen-1-yl]-3-(2-methoxy-5-trifluoromethoxy-phenyl)-urea -continued

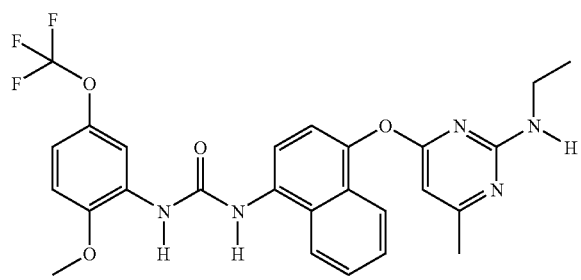
1-(2-Methoxy-5-trifluoromethoxy-phenyl)-3-[4-(6-methyl-2-ethylamino-pyrimidin-4-yloxy)-naphthalen-1-yl]-urea

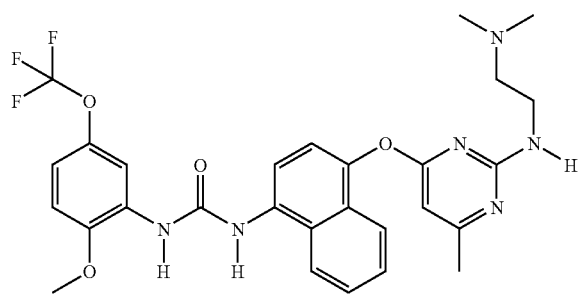
1-{4-[2-(2-Dimethylamino-ethylamino)-6-methyl-pyrimidin-4-yloxy]-naphthalen-1-yl}-3-(2-methoxy-5-trifluoromethoxy-phenyl)-urea

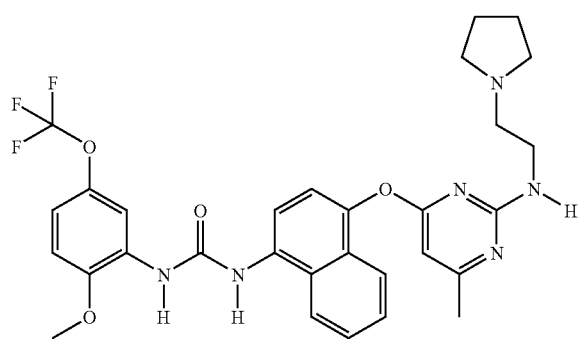
1-(2-Methoxy-5-trifluoromethoxy-phenyl)-3-{4-[6-methyl-2-(2-pyrrolidin-1-yl-ethylamino)-pyrimidin-4-yloxy]-naphthalen-1-yl}-urea

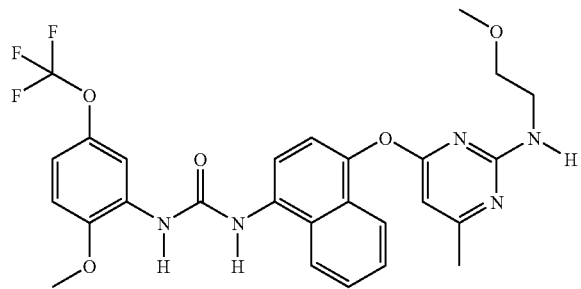
1-{4-[2-(2-Methoxy-ethylamino)-6-methyl-pyrimidin-4-yloxy]-naphthalen-1-yl}-3-(2-methoxy-5-trifluoromethoxy-phenyl)-urea

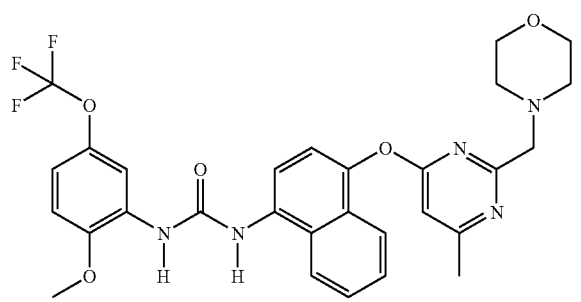
1-(2-Methoxy-5-trifluoromethoxy-phenyl)-3-[4-(6-methyl-2-morpholin-4-ylmethyl-pyrimidin-4-yloxy)-naphthalen-1-yl]-urea

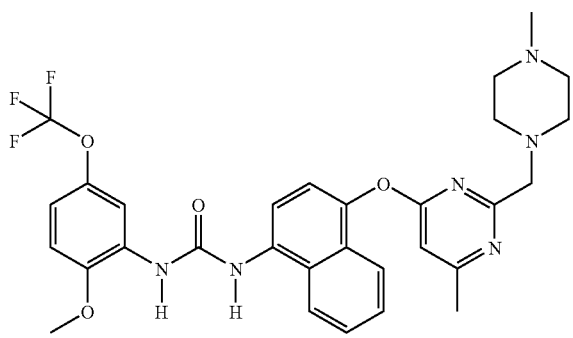

1-(2-Methoxy-5-trifluoromethoxy-phenyl)-3-{4-[6-methyl-2-(4-methyl-piperazin-1-ylmethyl)-pyrimidin-4-yloxy]-naphthalen-1-yl}-urea

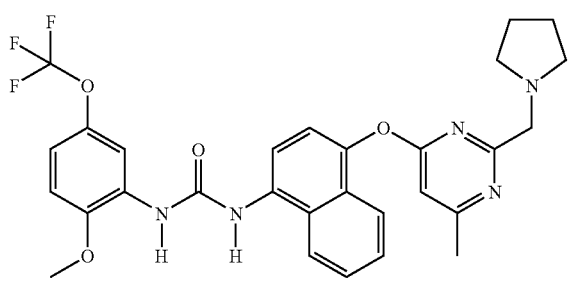

1-(2-Methoxy-5-trifluoromethoxy-phenyl)-3-[4-(6-methyl-2-pyrrolidin-1-ylmethyl-pyrimidin-4-yloxy)-naphthalen-1-yl]-urea

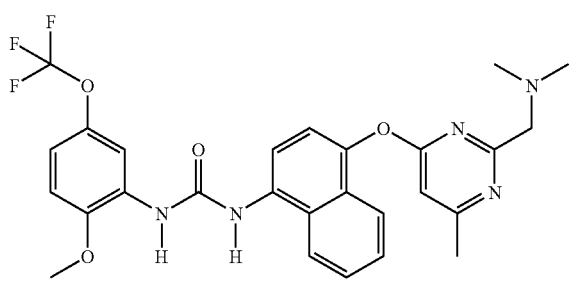

1-[4-(2-Dimethylaminomethyl-6-methyl-pyrimidin-4-yloxy)-naphthalen-1-yl]-3-(2-methoxy-5-trifluoromethoxy-phenyl)-urea

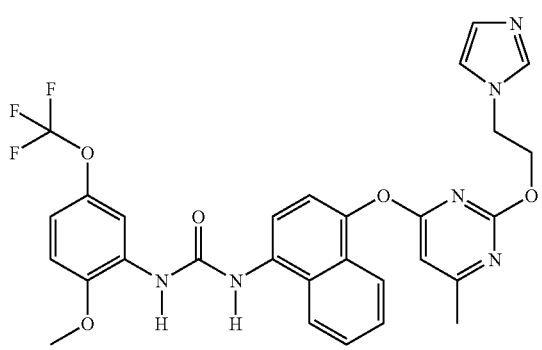

1-{4-[2-(2-Imidazol-1-yl-ethoxy)-6-methyl-pyrimidin-4-yloxy]-naphthalen-1-yl}-3-(2-methoxy-5-trifluoromethoxy-phenyl)-urea

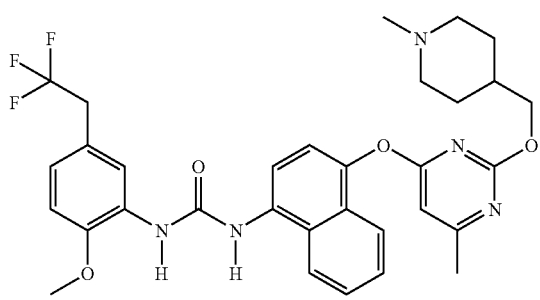

1-[2-Methoxy-5-(2,2,2-trifluoro-ethyl)-phenyl]-3-{4-[6-methyl-2-(1-methyl-piperidin-4-ylmethoxy)-pyrimidin-4-yloxy]-naphthalen-1-yl}-urea

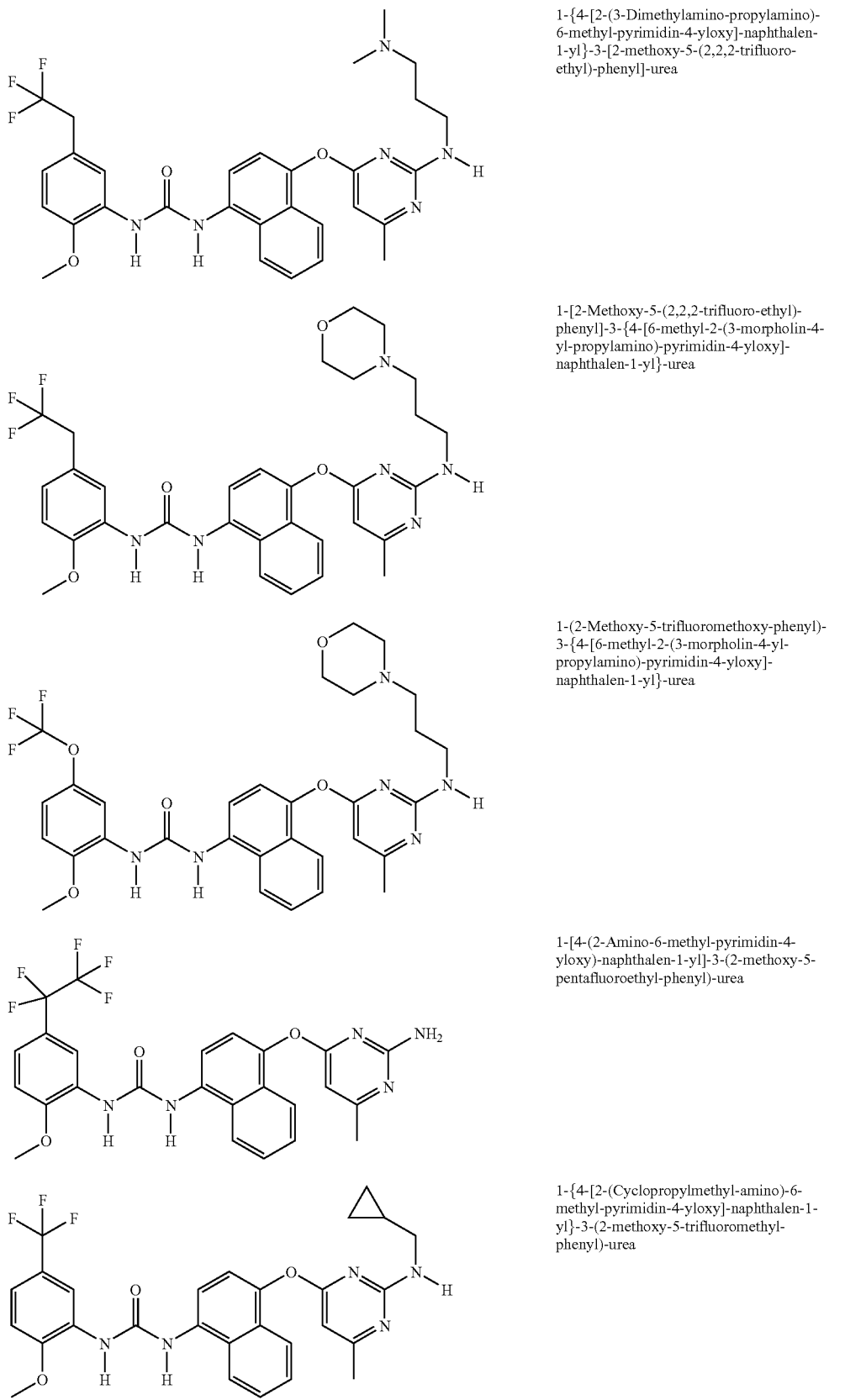

1-{4-[2-(3-Dimethylamino-propylamino)-6-methyl-pyrimidin-4-yloxy]-naphthalen-1-yl}-3-[2-methoxy-5-(2,2,2-trifluoro-ethyl)-phenyl]-urea 1-[2-Methoxy-5-(2,2,2-trifluoro-ethyl)-phenyl]-3-{4-[6-methyl-2-(3-morpholin-4-yl-propylamino)-pyrimidin-4-yloxy]-naphthalen-1-yl}-urea 1-(2-Methoxy-5-trifluoromethoxy-phenyl)-3-{4-[6-methyl-2-(3-morpholin-4-yl-propylamino)-pyrimidin-4-yloxy]-naphthalen-1-yl}-urea 1-[4-(2-Amino-6-methyl-pyrimidin-4-yloxy)-naphthalen-1-yl]-3-(2-methoxy-5-pentafluoroethyl-phenyl)-urea 1-{4-[2-(Cyclopropylmethyl-amino)-6-methyl-pyrimidin-4-yloxy]-naphthalen-1-yl}-3-(2-methoxy-5-trifluoromethyl-phenyl)-urea -continued

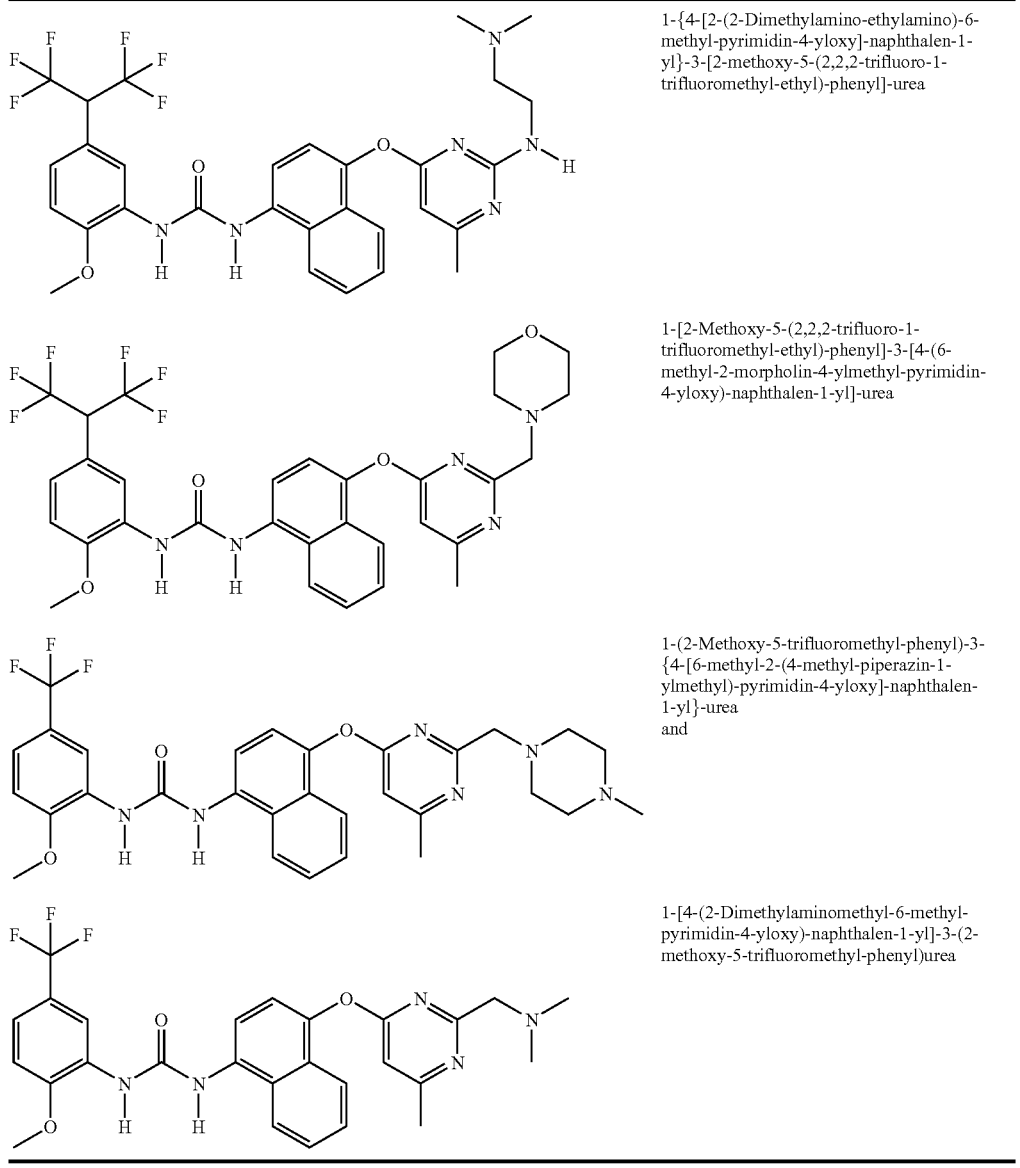

1-{4-[2-(2-Dimethylamino-ethylamino)-6-methyl-pyrimidin-4-yloxy]-naphthalen-1-yl}-3-[2-methoxy-5-(2,2,2-trifluoro-1-trifluoromethyl-ethyl)-phenyl]-urea 1-[2-Methoxy-5-(2,2,2-trifluoro-1-trifluoromethyl-ethyl)-phenyl]-3-[4-(6-methyl-2-morpholin-4-ylmethyl-pyrimidin-4-yloxy)-naphthalen-1-yl]-urea 1-(2-Methoxy-5-trifluoromethyl-phenyl)-3-{4-[6-methyl-2-(4-methyl-piperazin-1-ylmethyl)-pyrimidin-4-yloxy]-naphthalen-1-yl}-urea
and 1-[4-(2-Dimethylaminomethyl-6-methyl-pyrimidin-4-yloxy)-naphthalen-1-yl]-3-(2-methoxy-5-trifluoromethyl-phenyl)urea or the pharmaceutically acceptable acids, esters, salts or isomers thereof.

In another embodiment, the invention provides the following compounds:

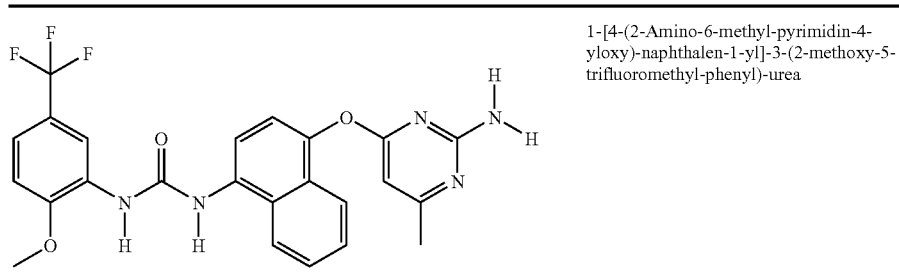

1-[4-(2-Amino-6-methyl-pyrimidin-4-yloxy)-naphthalen-1-yl]-3-(2-methoxy-5-trifluoromethyl-phenyl)-urea

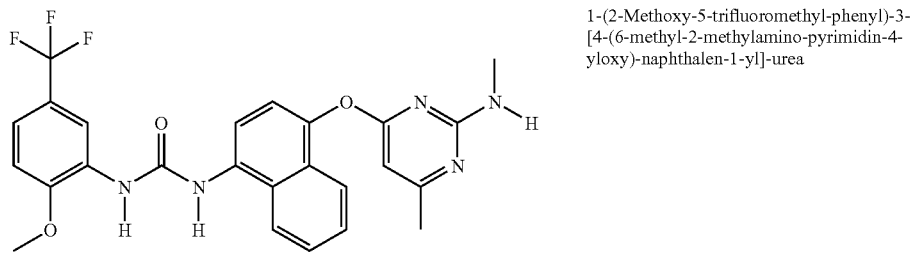
1-(2-Methoxy-5-trifluoromethyl-phenyl)-3-[4-(6-methyl-2-methylamino-pyrimidin-4-yloxy)-naphthalen-1-yl]-urea

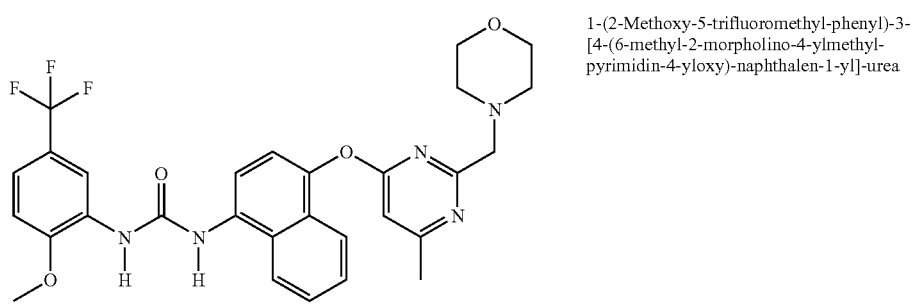
1-(2-Methoxy-5-trifluoromethyl-phenyl)-3-[4-(6-methyl-2-morpholino-4-ylmethyl-pyrimidin-4-yloxy)-naphthalen-1-yl]-urea

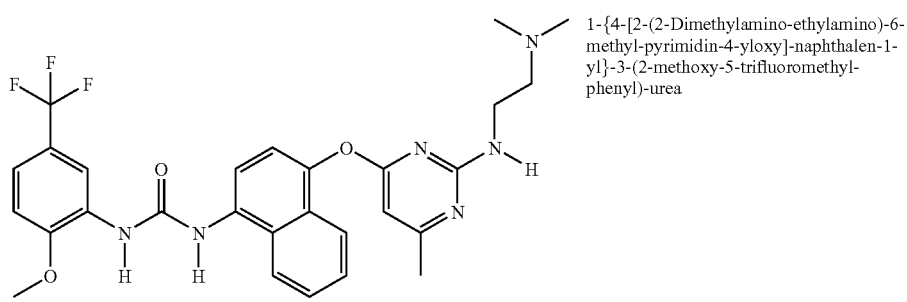
1-{4-[2-(2-Dimethylamino-ethylamino)-6-methyl-pyrimidin-4-yloxy]-naphthalen-1-yl}-3-(2-methoxy-5-trifluoromethyl-phenyl)-urea

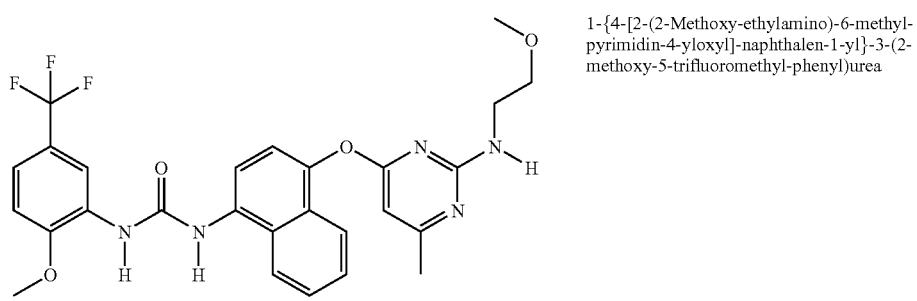
1-{4-[2-(2-Methoxy-ethylamino)-6-methyl-pyrimidin-4-yloxyl]-naphthalen-1-yl}-3-(2-methoxy-5-trifluoromethyl-phenyl)urea

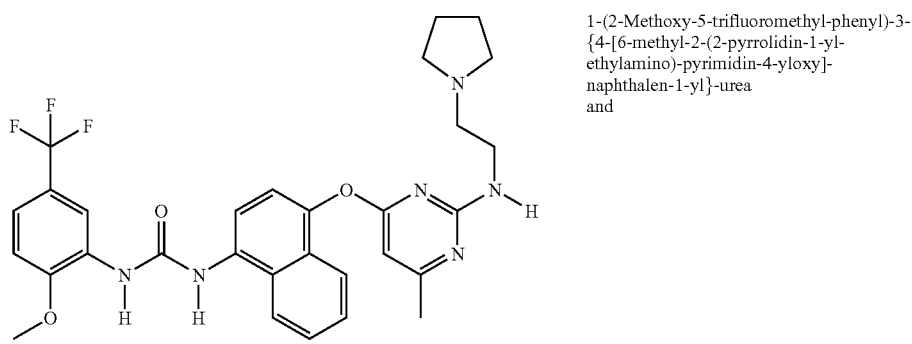
1-(2-Methoxy-5-trifluoromethyl-phenyl)-3-{4-[6-methyl-2-(2-pyrrolidin-1-yl-ethylamino)-pyrimidin-4-yloxy]-naphthalen-1-yl}-urea
and -continued

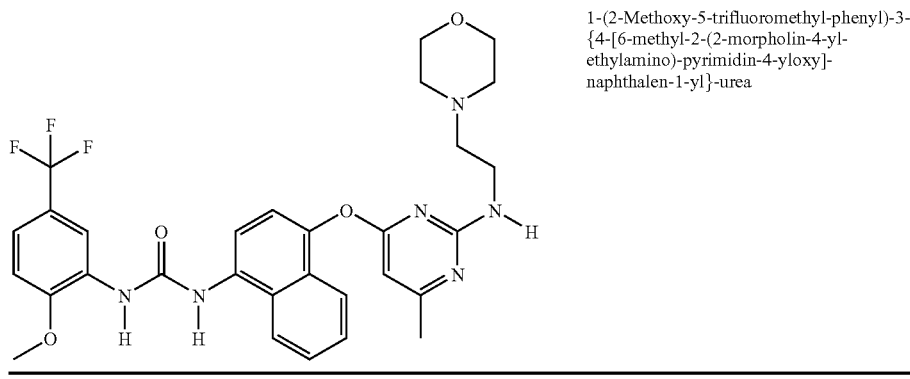

1-(2-Methoxy-5-trifluoromethyl-phenyl)-3-{4-[6-methyl-2-(2-morpholin-4-yl-ethylamino)-pyrimidin-4-yloxy]-naphthalen-1-yl}-urea or the pharmaceutically acceptable acids, esters, salts or isomers thereof.

In all the compounds disclosed hereinabove in this application, in the event the nomenclature is in conflict with the structure, it shall be understood that the compound is defined by the structure.

Of particular importance according to the invention are compounds of formula (I), wherein $R_1$, $R_2$, $R_3$, W and X have the meaning indicated, for use as pharmaceutical compositions with an anti-cytokine activity.

The invention also relates to the use of a compound of formula (I), wherein $R_1$, $R_2$, $R_3$, W and X have the meaning indicated, for preparing a pharmaceutical composition for the treatment and/or prevention of a cytokine mediated disease or condition.

The invention also relates to pharmaceutical preparations, containing as active substance one or more compounds of general formula (I), wherein $R_1$, $R_2$, $R_3$, W and X have the meanings indicated, or the pharmaceutically acceptable derivatives thereof, optionally combined with conventional excipients and/or carriers.

The invention includes the use of any compounds of described above containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "C1-3 alkoxy" is a C1-3 (not an example used) alkyl with a terminal oxygen, such as methoxy, ethoxy, propoxy. All alkyl, alkenyl and alkynyl groups shall be understood as being branched or unbranched where structurally possible and unless otherwise specified. Other more specific definitions are as follows:

Carbocycles include hydrocarbon rings containing from three to ten carbon atoms. These carbocycles may be either aromatic and non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used inerchangeably.

In all alkyl groups or carbon chains one or more carbon atoms can be optionally replaced by heteroatoms: O, S or N. It shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in defintions such as but not limited to: alkoxycarbonyl, acyl, amido and thioxo.

Each aryl or heterocycle unless otherwise specified includes it's partially hydrogenated derivative. For example, pyrrolidinyl may include pyrrolinyl, phenyl may include it's hydrogenated derivatives such as cyclohexenyl. Other partially or fully hydrogenated derivatives will be apparent to one of ordinary skill in the art.

As used herein, "nitrogen" and "sulfur" include any oxidized form of nitrogen and sulfur and the quatemized form of any basic nitrogen.

The term "halogen" as used in the present specification shall be understood to mean bromine, chlorine, fluorine or iodine, preferably fluorine. The definitions "partially or fully halogenated"; "substituted by one or more halogen atoms", includes for example, mono, di or tri halo derivatives on one or more carbon atoms. All alkyl, alkoxy, aryl moities shall be understood to be optionally halogenated unless otherwise indicated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts.

In addition, within the scope of the invention is use of prodrugs of compounds of the formnula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

Methods of Use

In accordance with the invention, there are provided novel methods of using the compounds of the formula (I). The compounds disclosed therein effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds are useful for the treatment of diseases and conditions as described in the Background section, including the following conditions and diseases:

osteoarthritis, atherosclerosis, contact dermatitis, bone resorption diseases, reperfusion injury, asthma, multiple sclerosis, Guillain-Barre syndrome, Crohn's disease, ulcerative colitis, psoriasis, graft versus host disease, systemic lupus erythematosus and insulin-dependent diabetes mellitus, rheumatoid arthritis, toxic shock syndrome, Alzheimer's disease, toxic shock syndrome, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis, complications including restenosis following percutaneous transluminal coronary angioplasty, traumatic arthritis, sepsis, chronic obstructive pulmonary disease and congestive heart failure.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. The above described compounds may be physically combined with the conventional therapeutics or other adjuvants into a single pharmaceutical composition. Reference is this regard may be made to Cappola et al.: U.S. patent application Ser. No. 09/902,822, PCT/US 01/21860 and U.S. provisional application No. 60/313,527, each incorporated by reference herein in their entirety. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. Reference in this regard may also be made to U.S. provisional application No. 60/339,249. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

General Synthetic Methods

The invention additionally provides for methods of making the compounds of the formula (I). The compounds of the invention and the intermediates in the scheme below may be prepared by the general methods and examples presented below, and methods known to those of ordinary skill in the art. Further reference in this regard may be made to U.S. Pat. No. 6,297,381, U.S. application Ser. Nos. 09/505,582, 09/484,638, 09/735,160, 09/902,085, 09/698,442, 09/834,797, 09/611,109, 10/147,675, U.S. provisional application Nos. 60/206,327, 60/216,283, 60/295,909, 60/291,425, 60/283,642 and 60/268,841. Each of the aforementioned are incorporated herein by reference in their entirety.

The compounds of the invention may be prepared by Method A, B, C or D as illustrated in Scheme I. In Scheme I Ar has the meaning:
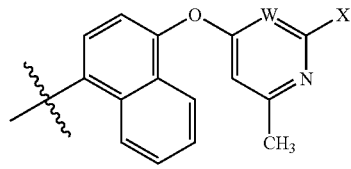
Scheme I
Method A
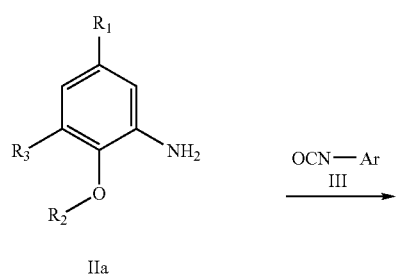
Method B
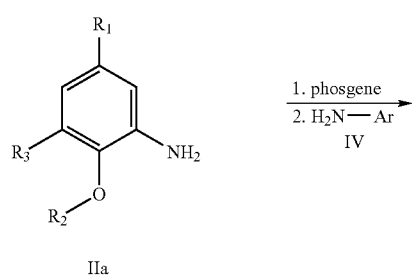
Method C
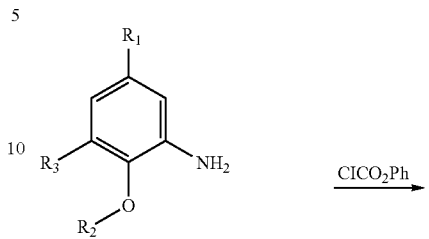
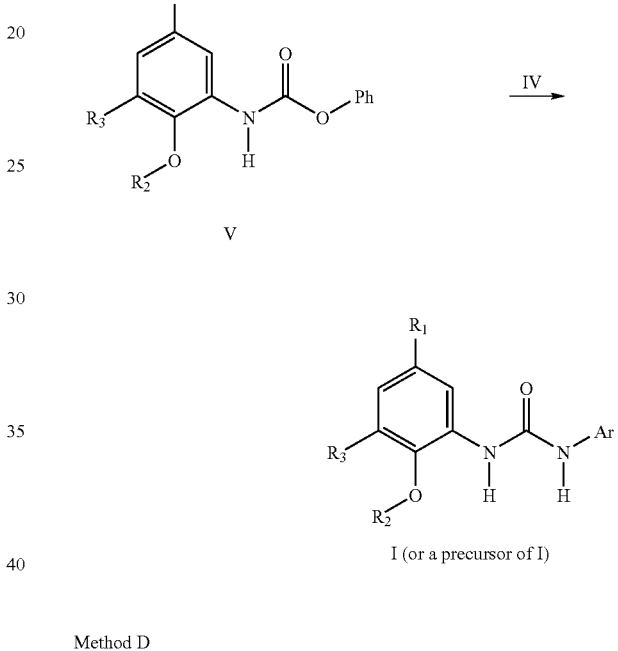
Method D
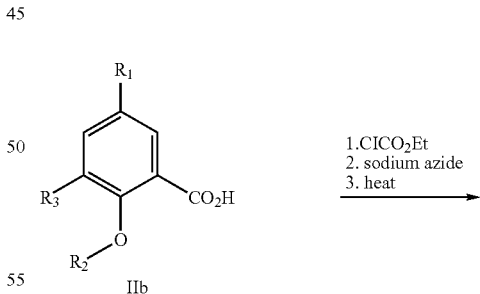
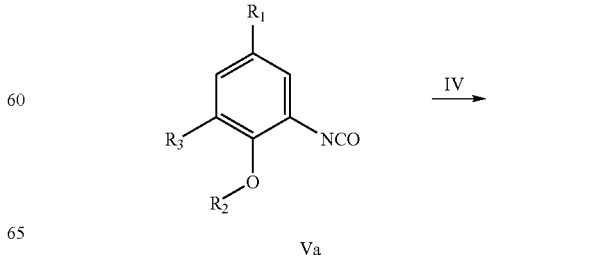

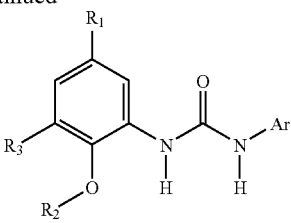

I (or a precursor of I)

In Method A, a mixture of an arylamine of formula Ia and an arylisocyanate of formula III is dissolved in a non-protic, anhydrous solvent such as THF, ether, toluene, dioxane or ethyl acetate. The preferred solvent is THF. The mixture is stirred at between 0-45° C., preferably at 25° C., for 2-24 h, and the volatiles are removed. Purification of the residue can be accomplished by recrystallization from an appropriate solvent such as ethyl acetate/hexanes, ethyl acetate/methanol, THF/petroleum ether or ethanol/water or by silica gel chromatography, using for example, hexanes and ethyl acetate as eluents, providing the product of formula I or precursors thereof.

In Method B, an arylamine of formula Ia is dissolved in a halogenated solvent, such as dichloromethane, chloroform or dichloroethane. The preferred solvent is dichloromethane. The mixture is diluted with aqueous alkali, such as sodium bicarbonate or potassium carbonate, cooled in an ice bath and phosgene is added. The mixture is vigorously stirred for 5-40 min. The organic layer is dried, with agents such as $MgSO_4$ or $Na_2SO_4$, and the volatiles removed to provide the corresponding isocyanate. The isocyanate and arylamine IV are mixed in a non-protic, anhydrous solvent such as THF, ether, toluene, dioxane, dichloromethane or ethyl acetate. The preferred solvent is THF. The mixture is stirred at between about 0-45° C., preferably at 25° C., for 2-24 h, and the volatiles are removed. Purification of the residue by recrystallization or by silica gel chromatography, as above, provides the product of formula I or precursors thereof.

In Method C, an arylamine of formula Ia is dissolved in a suitable halogenated solvent such as dichloromethane, chloroform or dichloroethane. The preferred solvent is dichloromethane. A suitable base such as triethylamine may be added, followed by an alkyl or aryl chloroformate, such as t-butyl chloroformate or phenyl chloroformate (shown). The mixture is stirred at between 0-85° C., preferably at reflux temperature, for 2-24 h, and the volatiles are removed providing carbamate V. The carbamate and arylamine IV are mixed in a non-protic, anhydrous solvent such as THF, ether, toluene, dioxane, dichloromethane or ethyl acetate. The preferred solvent is THF. The mixture is stirred at between 0-110° C., preferably at reflux temperature, for 2-24 h, and the volatiles are removed. Purification of the residue as above provides the product of formula I or precursors thereof.

In Method D, an aromatic carboxylic acid is dissolved in a non-protic solvent, such as THF or diethyl ether, and an inorganic base, such as triethyl amine is added and the mixture is cooled to −30-0° C., with the preferred temperature being −10° C. An alkyl chloroformate, such as ethyl chloroformate, is added dropwise and the resulting mixture stirred at below room temperature, such as 0° C. for 1-3 hours. A solution of sodium azide in water is added and the mixtiure stirred between 1-3 hours, diluted with toluene and the organic layer dried and reduced in volume. This mixture is heated at reflux for 1-4 hours, cooled to room temperature to give isocyanate (Vb) which can be reacted with amine (IV) to give product of formula I or precursors thereof.

SYNTHETIC EXAMPLES

Example 1

Synthesis of 1-{4-[2-(2-dimethylamino-ethylamino)-6-methyl-pyrimidin-4-yloxy]-naphthalen-1-yl}-3-(2-methoxy-5-trifluoromethyl-phenyl)-urea

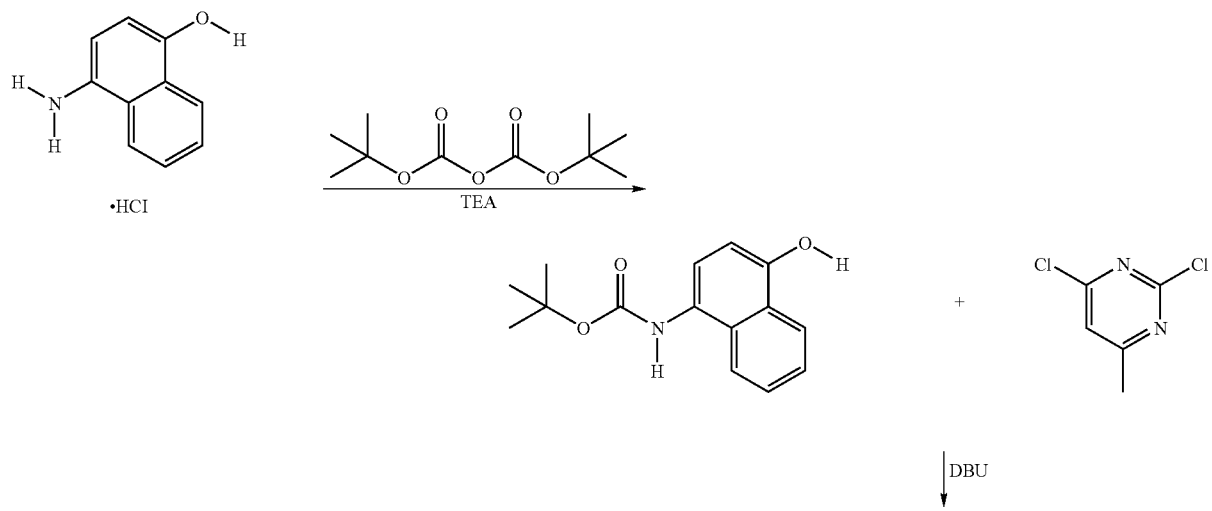

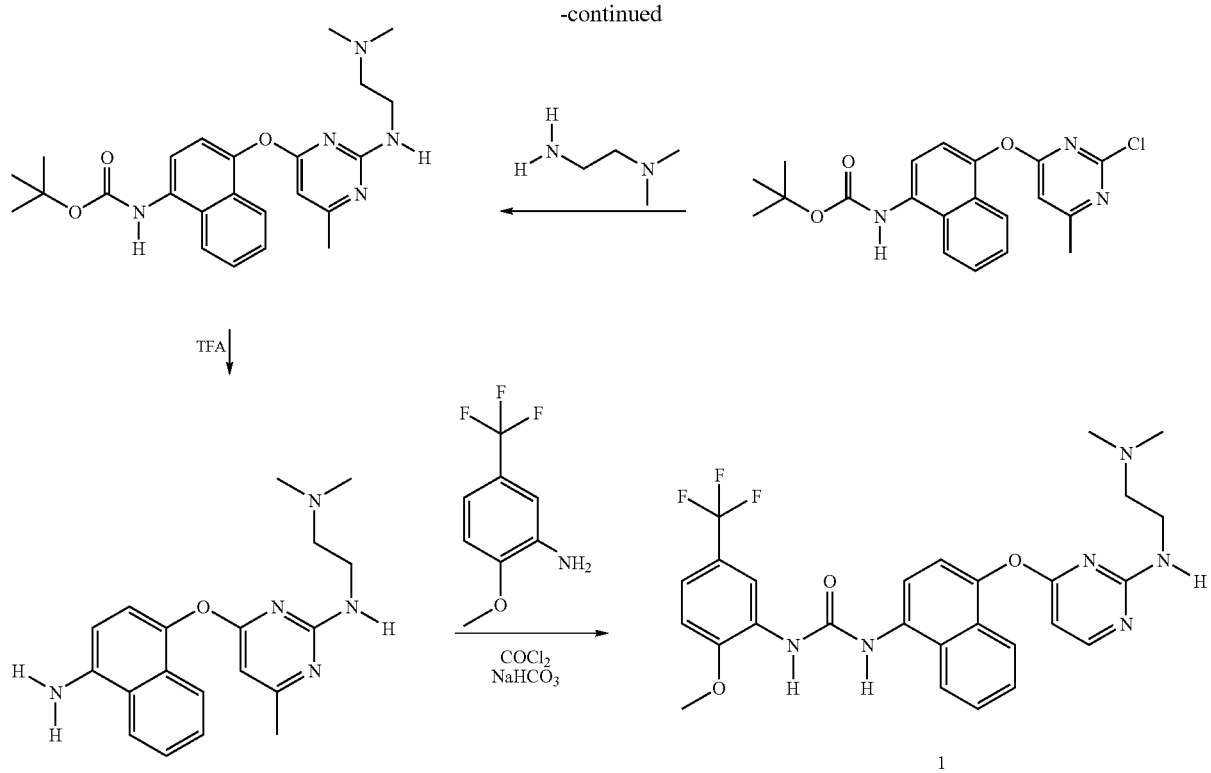

4-Aminonaphthalen-1-ol hydrochloride (50.0 g, 0.256 mol) was suspended in 500 mL THF under $N_2$. Triethylamine (39.2 mL, 0.281 mol) was added dropwise from an addition funnel. The reaction was stirred for 30 min. Boc anhydride (55.79 g, 0.256 mol), dissolved in 60 mL THF was added dropwise. The reaction was heated to reflux for 5 h and then cooled first to room temperature first and then in a dry ice-acetone bath. The triethylamine HCl salt was filtered off and the precipitate was washed with small portions of THF. The filtrate was concentrated in vacuo leaving a thick brown oil. About 500 mL dichloroethane was added tom the oil and the solution was treated with a small amount of activated charcoal and then filtered through diatomaceous earth, using cold dichloroethane to wash the cake. The filtate was concentrated in vacuo providing the desired Boc-aminonaphthol product as a purple-browish solid (50 g).

The above Boc-aminonaphthol (40.0 g, 0.154 mol) was suspended in 250 mL acetonitrile under nitrogen in a 1000 mL three-neck round bottom flask. 1,8-Diazabicyclo[5.4.0]undec-7-ene (DBU) (23.5 mL, 0.154 mol) dissolved in a small amount of acetonitrile was added dropwise to the suspension. The solids dissolved to form a clear, green-brownish solution. Once the addition was completed, 2,4-dichloro-6-methylpyrimidine (25.62 g, 0.154 mol) in 40 mL acetonitrile was added in one portion to the reaction flask (washed with a little more $CH_3CN$). The reaction mixture was heated to reflux for 4 h, then cooled in an ice-acetone bath. The reaction was filtered to obtain a beige colored powder which was dried to provide 37.8 g (65%) of the desired chloro-pyrimidyl ether.

The above chloro-pyrimidyl ether (1.51 g, 3.91 mmol) was suspended in 20 mL anhydrous THF in a sealed tube. N,N-dimethylaminoethylamine (0.70 mL, 6.38 mmol) was then added and the mixture was brought to 90° C. and stirred for 10 h. The reaction was then allowed to cool to room temperature and was partitioned between EtOAc and diluted aqueous $NaHCO_3$ solution. The organic layer was separated and washed with brine, then dried ($Na_2SO_4$), filtered and concentrated in vacuo providing 1.71 g of the desired N,N-dimethylaminoethylamino-pyrimidine intermediate as a tan foam.

The above foam (1.71 g, ~3.91 mmol) was dissolved in 10 mL dichloromethane and 10 mL of trifluoroacetic acid were added. The mixture was stirred overnight at room temperature, then concentrated, partitioned between dichloromethane and saturated aqueous $NaHCO_3$ solution. The organic layer was dried ($Na_2SO_4$), filtered and concentrated in vacuo. The residue was purified by column chromatography on silica gel eluting with dichloromethane/MeOH/$NH_4OH$, providing 850 mg of the desired aminonaphthyl pyrimidine ether as a brown foam.

2-Methoxy-5(trifluoromethyl)aniline (commercially available) (109.7 mg, 0.551 mmol) was dissolved in 14 mL dichloromethane. Saturated aqueous $NaHCO_3$ solution (14 mL) was added and the mixture was cooled to 0° C. While stirring, the mixture was treated with phosgene by addition to the organic layer via syringe in one portion (0.95 mL, 1.92 mmol). The mixture was then stirred vigorously for 0.5 h, then the layers were separated. The aqueous layer was extracted once with dichloromethane and the combined organics were dried ($MgSO_4$), filtered and the dichloromethane was removed in vacuo. The isocyanate residue was added to the aminonaphthyl pyrimidine ether (186 mg, 0.551 mmol) in 2 mL anhydrous THF. The reaction mixture was left stirring at room temperature overnight and then concentrated in vacuo and triturated with ether to provide 250 mg of a pink solid. The product was purified by column chromatography on silica gel, eluting with 1:9:90 NH₄OH:MeOH:CH₂Cl₂ to provide 110 mg of the title compound as a tan foam.

Example 2

Synthesis of 1-[4-(2-Amino-6-methyl-pyrimidin-4-yloxy)-naphthalen-1-yl]-3-(2-methoxy-5-trifluoromethyl-phenyl)-urea The 4-methoxybenzylamino-pyrimidine intermediate from above (1.625 g, 3.34 mmol) was dissolved in 26.6 mL trifluoroacetic acid. The reaction was refluxed for 4 h, then stirred at 80° C. for another 3 h, cooled, then added slowly to a separatory funnel containing ~500 mL saturated NaHCO₃ aqueous solution and extracted twice with ethyl acetate. The combined organic extracts were washed with brine, dried (Na₂SO₄), filtered and concentrated in vacuo. The residue was purified by column chromatography on

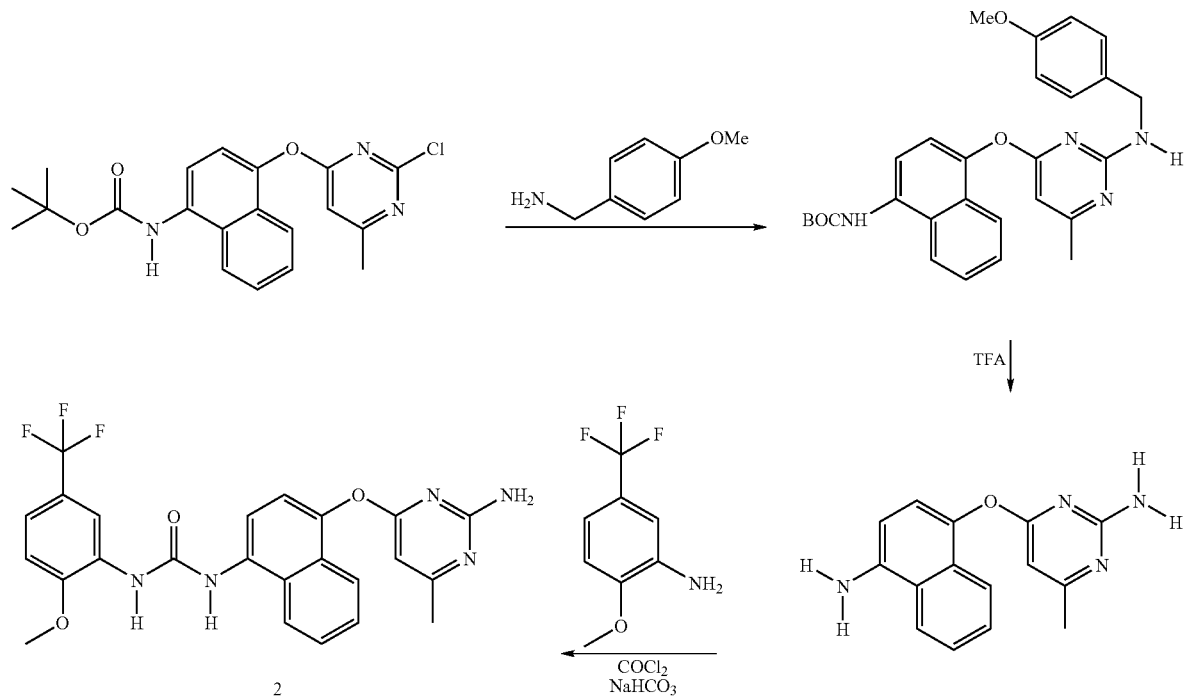

(4-Boc-amino-naphthyl)-(2-chloro-6-methyl-pyrimidinyl)-ether (see Example 1) (2.00 g, 5.18 mmol), 4-methoxybenzylamine (0.69 mL, 5.18 mmol) and triethylamine (0.73 mL, 5.18 mmol) were dissolved in 10 mL DMSO in a sealed tube. The tube was sealed and placed into a 95° C. oil bath. The reaction was stirred overnight, then cooled and ethyl acetate and water were added. The aqueous layer was washed twice with EtOAc. The organic extracts were combined, washed once with brine, dried (Na₂SO₄), filtered and concentrated in vacuo. The residue was dissolved in dichloromethane and purified by column chromatography on silica gel eluting with EtOAc/hexane, providing 0.625 g of the desired 4-methoxybenzylamino-pyrimidine intermediate as a bright yellow solid.

silica gel using MeOH/dichloromethane as eluent mixtures, providing 629 mg of the desired aminonaphtalene intermediate as a brown foam.

This product was coupled with isocyanate formed in situ to form the title compound using a procedure analogous to the one described in Example 1.

Example 3

Synthesis of 1-[4-(2,6-Dimethyl-pyrimidin-4-yloxy)-naphthalen-1-yl]-3-(2-methoxy-5-trifluoromethyl-phenyl)-urea

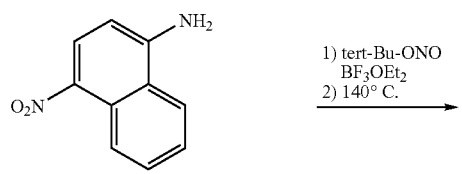

-continued

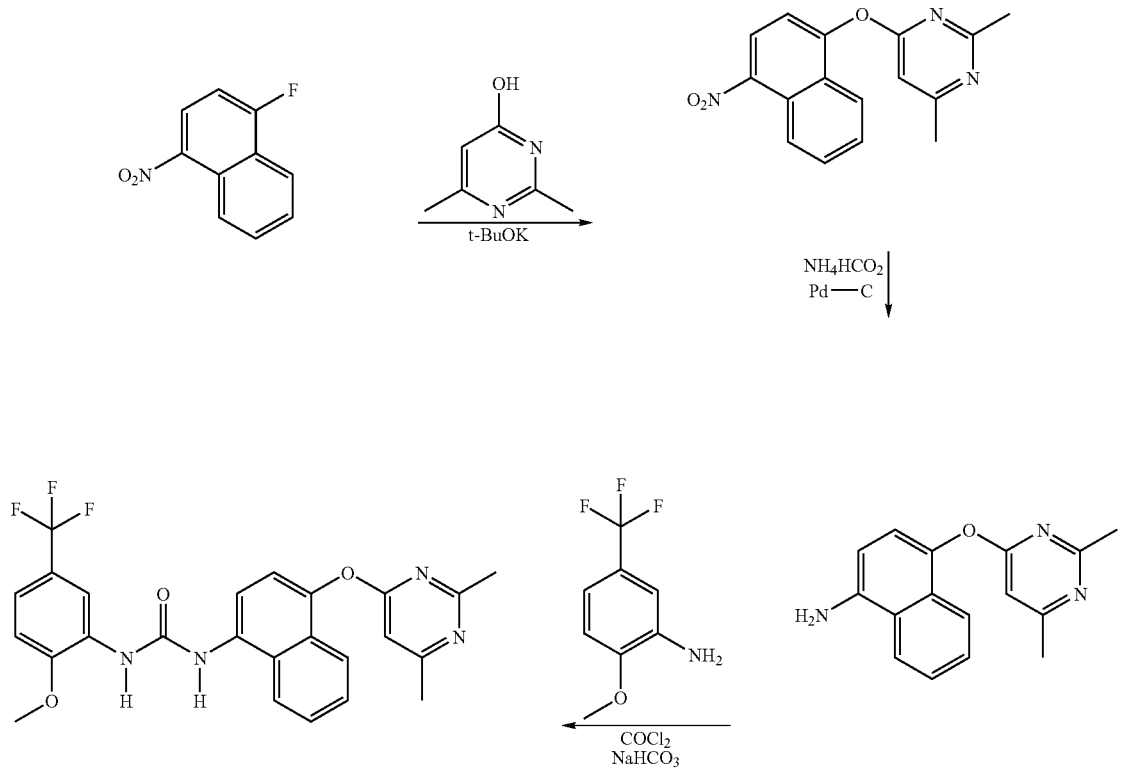

In a dry round-bottom flask under inert atmosphere and equipped with a magnetic stirrer bar was added boron trifluoride etherate (2.65 mL, 20.93 mmol, 1.5 equiv.). To this reagent cooled to 0° C. was then slowly added via syringe a solution on 4-nitro-1-naphthylamine (2.626 g, 13.95 mmol, 1 equiv.) in 39 mL anhydrous dimethoxyethane. The reaction was stirred for 15 min, and then a solution of tert-butyl nitrite (2.00 mL, 16.74 mmol, 1.2 equiv.) in 15 mL anhydrous dimethoxyethane was added dropwise via syringe. The mixture was allowed to reach room temperature and stir 1 h. It was then recooled to 0° C. without stirring. The precipitated green/gold diazonium tetrafluoroborate salt was collected by filtration (3.858 g, 13.44 mmol, 96%). It was used as is for the next step.

The nitronaphthalene diazonium tetrafluoroborate salt from above (3.448 g, 12.0 mmol, 1 equiv.) was suspended in 100 mL xylenes and heated to reflux for 1 h, then allowed to cool back to room temperature. Water was then added and the product extracted twice with ether. The combined extracts were dried (MgSO$_4$), filtered, and the solvents were removed in vacuo. The product 4-fluoro-1-nitronaphthalene was purified by column chromatography on silica gel using 10% EtOAc in hexanes as eluent providing 1.95 g of 4-fluoro-1-nitro-naphthalene (10.20 mmol, 85% yield).

2,4-dimethyl-6-hydroxy-pyrimidine (518 mg, 4.17 mmol) was dissolved in 7 mL anhydrous DMSO. Sodium tert-butoxide (382 mg, 3.98 mmol) was added in one portion and the mixture was stirred for 15 min at room temperature, until all the solids had dissolved. 4-Fluoro-nitronaphthalene (725 mg, 3.79 mmol) was then added in one portion and the mixture was heated to 65° C. and stirred for 2 h. The color immediately had changed to green. The reaction was then allowed to cool back to room temperature, and was left standing overnight. It was then quenched with water and extracted with EtOAc (3X). The combined organic extracts were washed twice with water and once with brine, dried (MgSO$_4$), filtered and concentrated in vacuo, providing 1.2 g of the desired ether intermediate as an orange solid that was used as is without further purification.

The ether intermediate from above (1.244 g, 4.21 mmol) was dissolved in 80 mL EtOH and 20 mL EtOAc. Ammonium formate (1.26 g, 20.0 mmol) and palladium-on-carbon catalyst (0.40 g) were added at room temperature, and the mixture was heated to 60° C. for 0.5-0.75 h. The reaction was allowed to cool back to room temperature and filtered through diatomaceous earth. The catalyst was washed with EtOAc, and the filtrates were concentrated in vacuo. The residue was purified on silica gel column eluting with EtOAc in hexanes eluent mixtures, providing 555 mg of the desired aminonaphthalene ether intermediate as a light purple foam.

This product was coupled the isocyanate formed in situ to form the title compound using a procedure analogous to the one described in Example 1.

Example 4

Synthesis of 1-(2-methoxy-5-trifluoromethyl-phenyl)-3-[4-(6-methyl-2-morpholin-4-ylmethyl-pyrimidin-4-yloxy)-naphthalen-1-yl]-urea

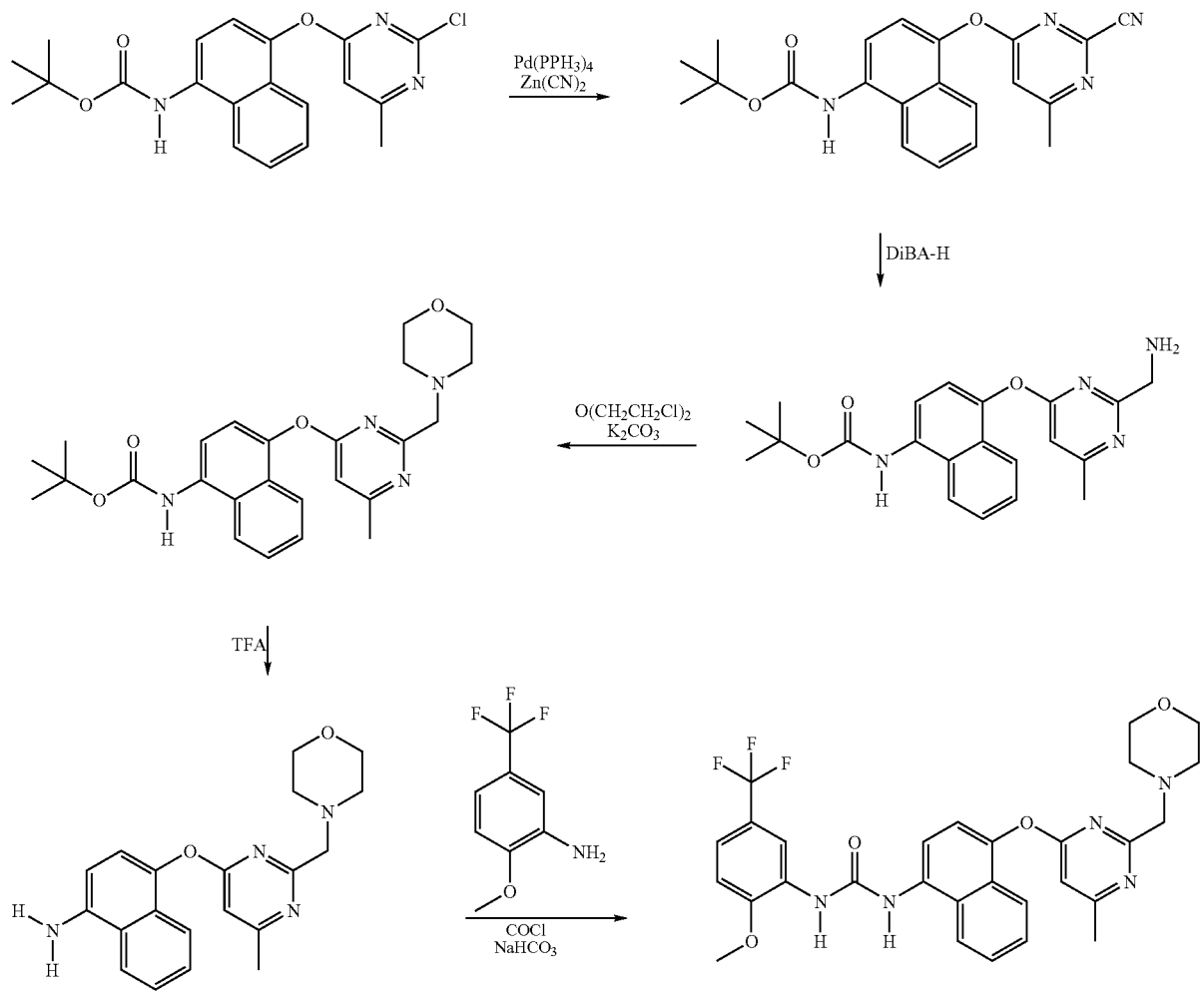

(4-Boc-amino-naphthyl)-(2-chloro-6-methyl-pyrimidinyl)-ether (see Example 1) (4.00 g, 10.37 mmol) was dissolved in 45 mL anhydrous DMF under an inert atmosphere, and treated with zinc cyanide (0.67 g, 5.71 mmol) and palladium catalyst (0.99 g, 0.86 mmol). The reaction was heated at 100-105° C. for 48 h, allowed to cool, then poured onto water and filtered. The resulting orange/tan solid was triturated twice in ether and filtered, providing 1.96 g of the desired 2-cyano-pyrimidinyl ether intermediate.

The 2-cyano-pyrimidinyl ether from above (1.95 g, 5.18 mmol) was suspended in 125 mL anhydrous toluene and cooled in an ice bath under an inert atmosphere. After stirring for 0.5 h, a solution of diisobutylaluminum hydride was added dropwise over 40 min.

The solution became homogeneous and bright orange/yellow. After stirring at 0° C. for 1 h, the reaction was quenched with sodium-potassium tartrate aqueous solution, stirred vigorously for 15 min then filtered through diatomaceous earth. The precipitate was washed with EtOAc and the organic filtrates were washed with brine and dried ($MgSO_4$).

The solution was filtered and concentrated in vacuo providing 1.08 g of the desired aminomethyl-pyrimidinyl ether as an orange foam, 1.08 g.

The aminomethyl-pyrimidinyl ether (1.88 g, 4.94 mmol) was suspended in 14.0 mL anhydrous 2-methoxyethyl ether. Potassium carbonate was added (0.81 g, 5.85 mmol), then a catalytic amount of sodium iodide and finally 2-chloroethyl ether (0.58 g, 4.95 mmol). The reaction was heated in a 110° C. bath for 12 h under an inert atmosphere, then allowed to cool. The reaction was then partitioned between water and dichloromethane, the pH adjusted to ~7 with ammonium chloride aqueous solution. The organics were dried with MgSO₄, filtered and concentrated in vacuo. The residue (containing some 2-methoxyethyl ether) was purified by column chromatography on silica gel using 0-10% MeOH in dichloromethane eluent mixtures to provide 610 mg of desired morpholinylmethyl-pyrimidinyl ether (main fraction, 1.35 mmol, 27%) as a brown foam. Also isolated was lower Rf material, which was the de-BOC product (~150 mg).

The morpholinylmethyl-pyrimidinyl ether from above (610 mg, 1.35 mmol) was dissolved in 5 mL dichloromethane and 5 mL trifluoroacetic acid were added. The mixture was stirred at room temperature overnight, then concentrated in vacuo, and partitioned between EtOAc and saturated aqueous NaHCO₃ solution. The EtOAc extracts were washed with water and brine, dried (Na2SO₄), filtered and concentrated in vacuo, providing 569 mg of the desired aminonaphthyl ether as a brown foam.

2-Methoxy-5-trifluoromethylaniline (335 mg, 1.75 mmol) was dissolved in 55 mL dichloromethane. Added 50 mL saturated aqueous NaHCO₃ solution, cooled the mixture to 0° C. and, while not stirring, treated with phosgene by addition to the organic layer via syringe in one portion (3.2 mL, 6.50 mmol). The mixture was then stirred vigorously for 20 min, then the layers were separated. The aqueous layer was extracted once with dichloromethane and the combined organics were dried (Na₂SO₄), filtered and the dichloromethane was removed in vacuo. The isocyanate residue in toluene was dissolved in 15 mL anhydrous THF and added to the aminonaphthyl ether from above (569 mg, 1.62 mmol) in 8 mL anhydrous THF, mixed with triethylamine (0.25 mL, 1.79 mmol, 1.1 equiv.). The reaction mixture was left stirring at room temperature overnight, then the reaction was concentrated in vacuo.

The residue was taken up in dichloromethane and purified by column chromatography on silica gel using MeOH in dichloromethane (0-10%) as eluents. The purification was repeated twice by column chromatography on silica gel using dichloromethane and 0-10% iso-PrOH as eluent to provide 199 mg of the title compound as a yellow foam.

Example 5

Synthesis of 1-(2-methoxy-5-trifluoromethoxy-phenyl)-3-{4-[6-methyl-2-(2-mormholin-4-yl-ethylamino)-pyrimidin-4-yloxy]-naphthalen-1-yl}-urea

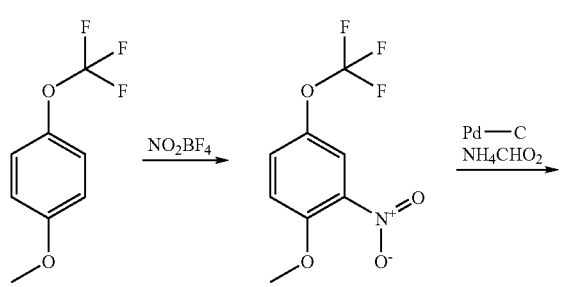

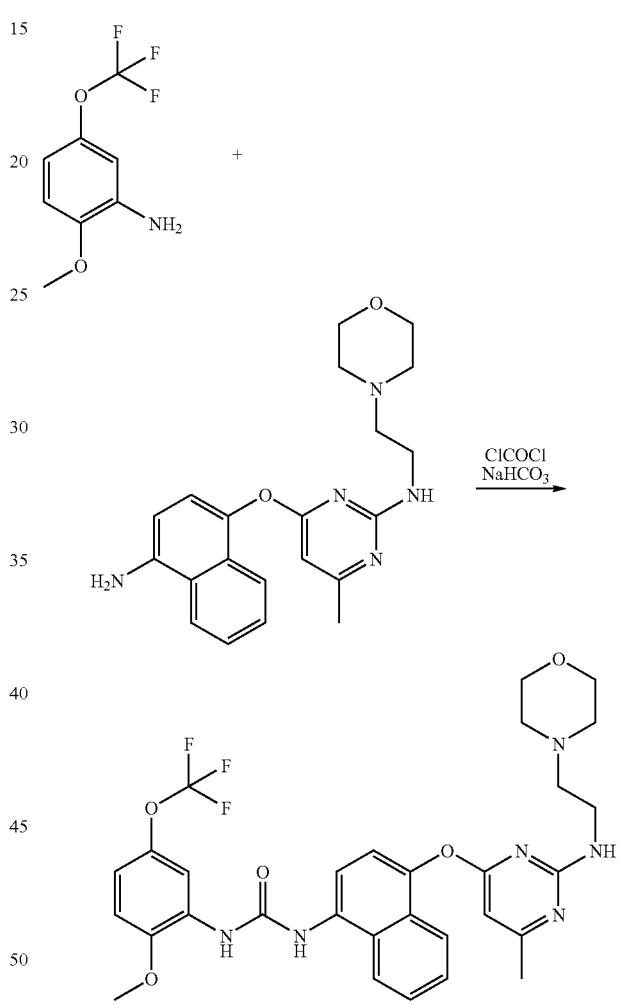

To 4-methoxy-trifluoromethoxybenzene (0.19 g, 0.001 mol) in 5 mL acetonitrile was added nitronium tetrafluoroborate (0.146 g, 0.001 mol) at room temperature. After about 6 h, another 0.25 equivs of nitronium tetrafluoroborate was added and the reaction stirred overnight. The reaction was then concentrated in vacuo, and the residue was partitioned between ether and water. The aqueous phase was washed twicw with ether, then the combined organic layers were washed with water, and dried over MgSO₄. The solvent was removed, resulting in a mobile oil. Kugelrohr distillation of the oil provided 0.2 g of the desired nitrated intermediate which was collected at 100-125° C.

The above nitrated intermediate (0.47 g, 0.002 mol) was added to a 3-neck micro round bottom flask, along with 10 mL acetonitrile. Ammonium formate (0.63 g, 0.010 mol) was added in a single portion (causes a yellow color), followed by Pd/C (0.106 g). The suspension was heated to reflux, and held for three h. An aliquot was removed and filtered through bed of diatomaceous earth (not yellow now). The bed was washed with some hot acetonitrile. TLC (4:1 hexanes:EtOAc) looked similar to starting material, but the spot darkened relatively quickly in the air (indicating aniline, not nitrobenzene). HPLC confirmed the starting material was consumed, with a new, more polar material formed. The reaction was worked up as per the aliquot, then the acetonitrile was removed in vacuo and the resulting oil was partitioned between ether and water. The aqueous layer was washed twice with ether, then the combined ether layers were dried over MgSO₄, filtered and concentrated to provide to an amber oil (0.41 g). Kugelrohr distillation of the material at ca. 125° C. provided the desired 2-methoxy-5-trifluoromethoxyaniline as a light amber oil.

The 2-methoxy-5-trifluoromethoxyaniline (0.041 g, 0.2 mmol) was dissolved in 5 mL dichloromethane in a 25 mL 3-neck micro round bottom flask and 5 mL of saturated aqueous NaHCO₃ was added. The reaction was cooled to −3° C. in ice-acetone bath. A phosgene/toluene solution was placed in an addition funnel, along with 2 mL dichloromethane and was added dropwise over 10 min. The reaction was stirred another 30 min, then the layers were separated. The aqueous layer was washed twice with dichloromethane, then the combined organics were dried over MgSO₄, then concentrated to a solution of the isocyanate in toluene.

The naphthylamine intermediate (0.076 g, mmol) was combined with THF in a 25 mL 3-neck micro flask. The solution was cooled to −5° C. in an ice-acetone bath and the isocyanate solution from above was transferred with THF into an addition funnel and added dropwise over 10 min, and the reaction stirred at room temperature overnight. The solvent was then removed in vacuo and the residue directly run on RP-HPLC to afford the title compound.

Example 6

Synthesis of 2-methoxy-5-(2,2,2-trifluoro-1-trifluoromethyl-ethyl)-phenylamine

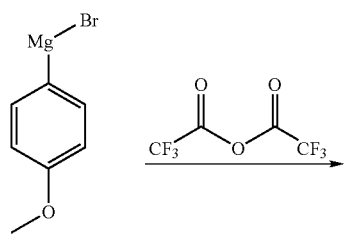

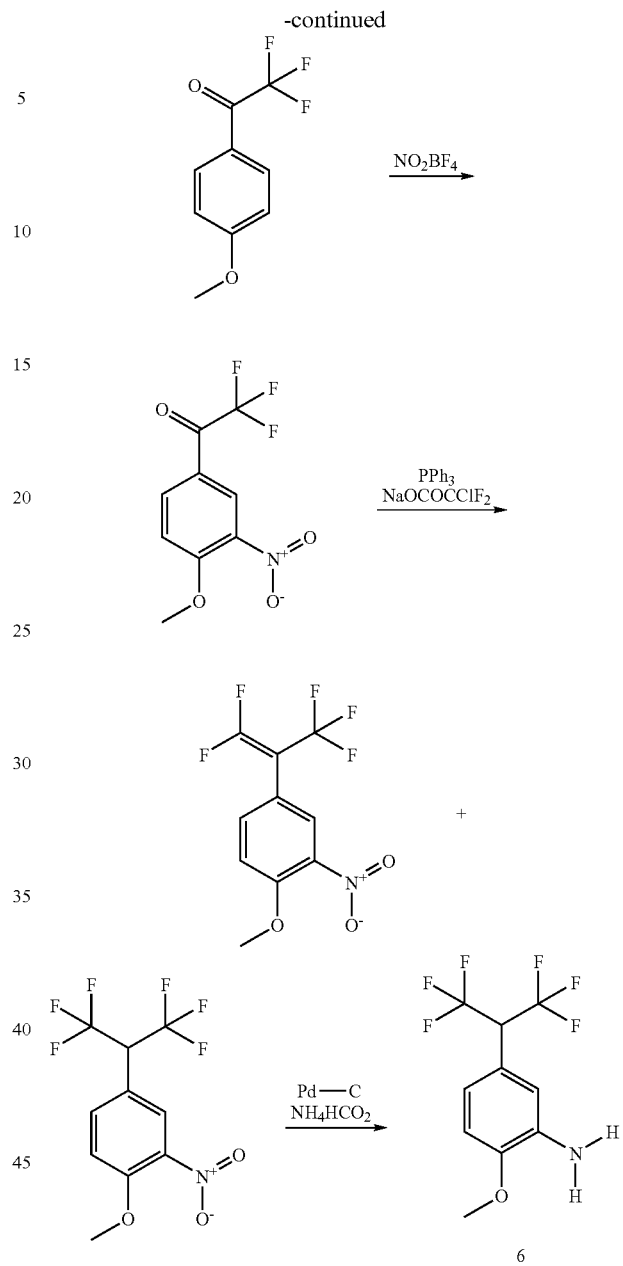

Trifluoroacetic anhydride (30 mL, 0.201 mol) was placed in a 500 mL 3-neck round bottom flask under nitrogen and cooled to −5° C. in ice/acetone bath. A 0.5 M solution of 4-methoxyphenyl magnesium bromide in THF (200 mL, 0.100 mol) was added dropwise (over an hour), maintaining temperature less than 5° C. After the addition was complete, the reaction was stirred at room temperature overnight, then heated to reflux for 2 h. The THF solvent was removed in vacuo and the residue was partitioned between ether and saturated ammonium chloride aqueous solution. The layers were separated and the organic layer was washed with 1 N HCl, then 1 N NaOH, then water, then brine, and then dried over MgSO₄ and concentrated in vacuo. The resulting oil was purified by Kugelrohr distillation at 150° C. to provide15 g of 4-methoxytrifluoroacetophenone as a bright yellow oil, 75% of theory.

4-Methoxytrifluoroacetophenone (6.10 g, 0.030 mol) was placed in a 100 mL 3-neck flask under N$_2$, along with 30 mL acetonitrile. While cooling on an ice bath, nitronium tetrafluoroborate (4.40 g, 0.033 mol) was added in portions. An initial yellow color turned to brown. After addition was complete, the reaction was stirred overnight, then concentrated to a red/brown oil which was partitioned between ether and water. The ether was washed twice with water, then brine, then dried over MgSO$_4$, and concentrated to obtain 6.6 g of a dark oil. Kugelrohr distillation of the oil provided a yellow oil (fairly mobile) up to 125° C., then more material was collected from 125° C.-140° C. The latter material was less mobile and solidified providing the desired 4-methoxy-3-nitrotrifluoroacetophenone, suitable for the next step.

4-Methoxy-3-nitrotrifluoroacetophenone (1.993 g, 0.008 mol), the sodium salt of chlorodifluoromethylcarbonate salt (2.44 g, 0.016 mol), and triphenylphosphine (2.096 g, 0.008 mol) and 20 mL diglyme were combined in a 25 mL 3-neck micro round bottom flask. The reaction was heated and stirred overnight, using a controller to maintain the oil bath temperature at about 105° C. The reaction color turned to a red/brown solution. The temperature was brought up to 130° C. and the reaction stirred another 24 h.

The reaction mixture was then cooled to room temperature and poured onto hexanes. Upon sitting overnight, crystalline solid formed mixed with a dark gum. The solvent layer was decanted off, and the solid/gum was extracted twice with hexanes. The Combined organics were combined and washed with water. The hexane-soluble material was dried and concentrated in vacuo. The residue was purification by column chromatography on silica gel (10-->35% EtOAc in hexanes), providing both the pentafluoropropene and hexafluoropropane compounds (not fully separable).

The above pentafluoropropene—hexafluoropropane nitro compound mixture (0.30 g) was combined with 10 mL acetonitrile in a 25 mL 3-neck micro flask. Ammonium formate (0.378 g), and then the Pd/C (0.050 g), were added. The reaction was heated to reflux for 9 h. At the both 5 and 7 h timepoints 3 more equivalents of ammonium formate and 5 mol% of palladium-on-carbon were added. The reaction was then filtered hot through diatomaceous earth and washed with hot acetonitrile. The filtrates were concentrated to an oil and then partitioned between ether and water. The ether was washed with water, and then dried over MgSO$_4$ and concentrated to 0.28 g of a yellow oil.

The product was purified by column chromatography on silica gel (10-->35% EtOAc in hexanes eluent). Two fractions were isolated two fractions, a major which came out early, and a late-eluting minor. The title compound (210 mg) was the major, early eluting (less polar).

The title compound may be coupled to desired naphthylamines in a manner analogous to that described in the above examples.

Example 7

Synthesis of 1-[4-(2-amino-pyrimidin-4-yloxy)-naphthalen-1-yl]-3-(2-methoxy-5-pentafluoroethyl-phenyl)-urea

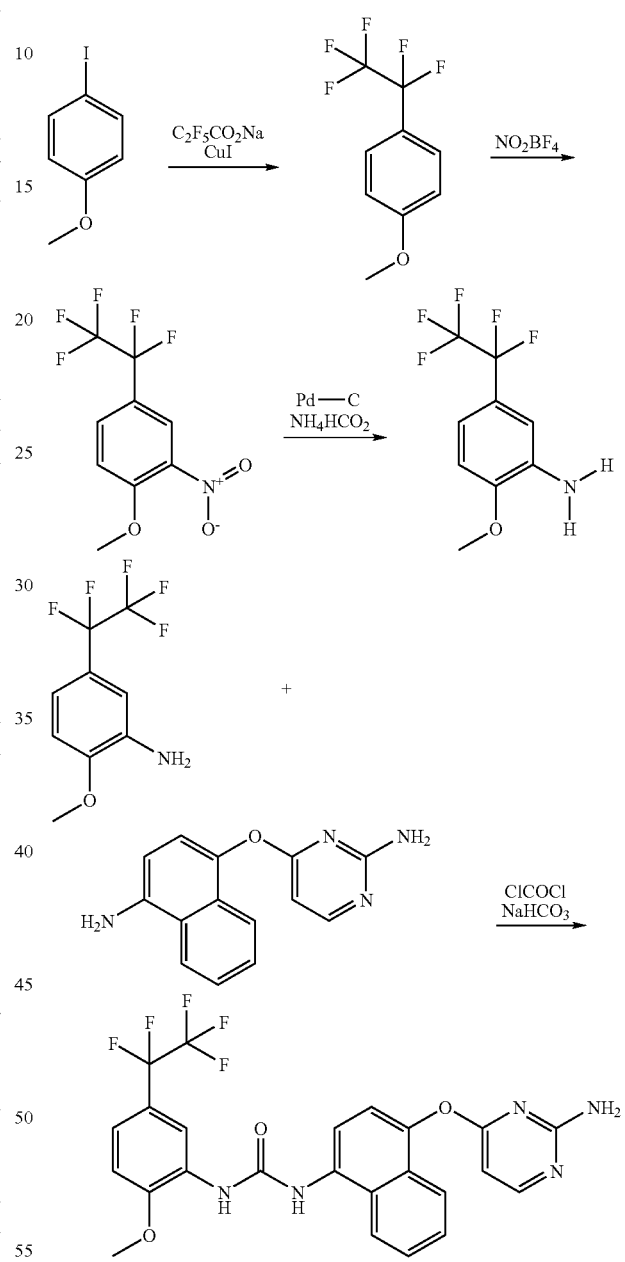

7

Iodoanisole (2.30 g, 0.010 mol), pentafluoropropionic acid sodium salt (3.70 g, 0.020 mol), and copper iodide (I) (3.80 g, 0.020 mol) were combined in 30 mL toluene and 90 mL DMF in a 250 mL, 3-neck round bottom flask equipped with a Dean Stark trap, condenser, thermometer, and nitrogen inlet. The reaction was heated in order to distill off the toluene (removal of water). The reaction was stirred a with magnetic stirrer, and the pot temperature raised to almost to 140° C., and the Dean Stark trap was heated with heat gun in order to maintain water removal. About 1.5 mL water was collected. The trap was removed and the reaction brought to reflux for 10 h, and then stirred another 6 h at room temperature.

The reaction suspension was added to to 200 mL water/ 200 ml EtOAc and then poured through a pad of diatomaceous earth to remove insolubles. The aqueous phase was washed twice with EtOAc. The combined EtOAc extracts were washed three times with large portions of water, then dried over MgSO$_4$. The solution was filtered and concentrated to a yellowish oil, which was subjected to Kugelrohr distillation, maintaining the temperature at or below 60° C. The desired 4-pentafluoroethylanisole was obtained as a clear, mobile liquid.

The above 4-pentafluoroethylanisole (1.131 g, 0.005 mol) was combined with 10 mL acetonitrile in a 3-neck micro flask. Nitronium tetrafluoroborate (0/797 g, 0.006 mol) was added in portions causing the clear solution to turn brown. The reaction was stirred overnight at room temperature, concentrated, and the product purified by Kugelrohr distillation. The desired 2-nitro-4-pentafluoroethylanisole (0.8 g, bp>80° C.) was obtained as a slightly yellow oil that formed a semi-solid after sitting 60 h.

The above 2-nitro-4-pentafluoroethylanisole (0.678 g, 0.003 mol) was added to a 25 mL 3-neck round bottom flask, along with 15 mL CH$_3$CN. Ammonium formate (0.950 g, 0.015 mol), and then the Pd/C (0.106 g) were added. The reaction was heated to reflux overnight, then filtered hot through bed of diatomaceous earth and washed with hot acetonitrile. The filtrate was concentrated in vacuo and the residue partitioned between EtOAc and water. The EtOAc was washed twice with water, then dried over MgSO$_4$ and concentrated. The residue was taken up in ether, and extracted with 1 N HCl, then water. The combined aqueous phase was then mixed with fresh ether, and then was made basic with 1 N NaOH. The aqueous phase was then washed with ether. The combined ether extracts were dried and concentrated to provide the desired aniline as a yellow oil.

The crude aniline from above (0.100 g, 0.41 mmol) was combined with 10 mL dichloromethane in a 25 mL 3-neck micro round bottom flask and cooled to −5° C. in an ice/acetone bath. Saturated NaHCO$_3$ aqueous solution (10 mL) was added to form a two-phase system. Phosgene/ toluene solution (0.847 mL, 0.002 mol) in 3 mL dichloromethane was added dropwise, and the reaction was stirred at ice temp another 40 min. The layers were separated and the aqueous washed twice with dichloromethane. The combined organic layers were dried over MgSO$_4$, and concentrated to a solution of crude isocyanate in toluene.

The naphthylamine intermediate (0.101 g, 0.40 mmol) was combined with 10 mL THF in 25 mL 3-neck micro round bottom flask and cooled to −5 in ° C. ice/acetone bath under nitrogen. The isocyanate/toluene solution from above in a few mL THF was added dropwise. The reaction was stirred on an ice bath for 30 min, then warmed to room temperature and then slowly heated to reflux for about 1 h. The reaction was then cooled and concentrated to a thick, red oil. The product was purified by column chromatography on silica gel eluting with 5% to 25% iPrOH in dichloromethane to provide 13 mg of the title compound as an off-white solid, melting point 220-230 (dec).

Example 8

Synthesis of N-(3-{3-[4-(2,6-dimethyl-2yrimidin-4-yloxy)-naphthalen-1-yl]-ureido}-2-methoxy-5-trifluoromethyl-phenyl)-methanesulfonamide

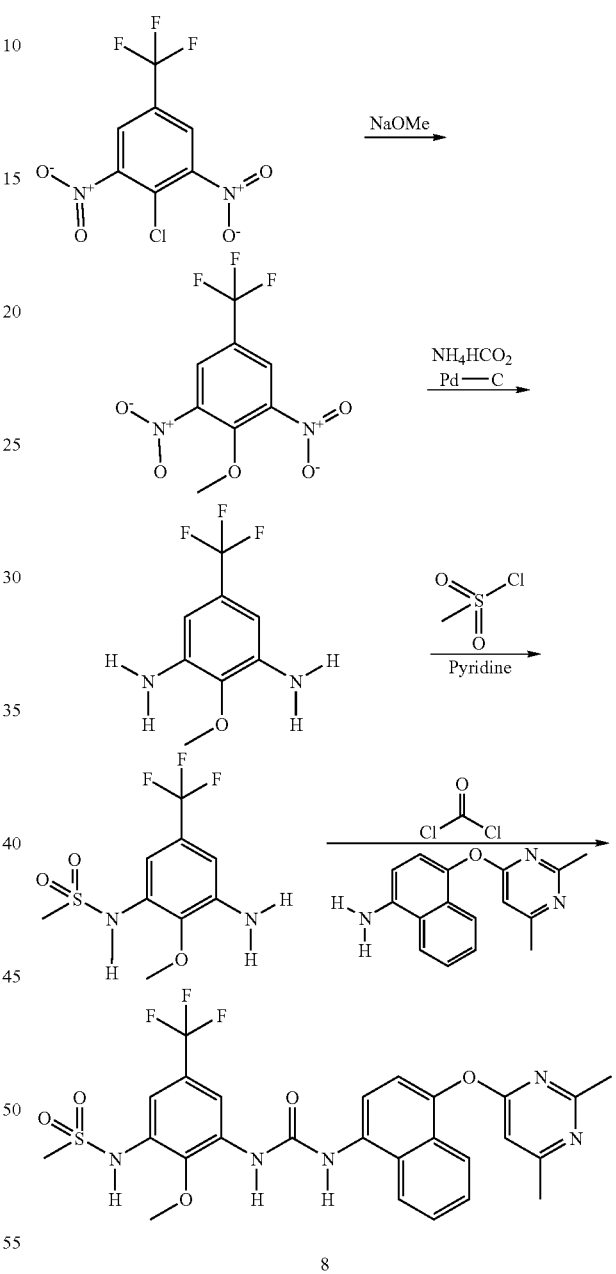

8

2-Chloro-1,3-dinitro-5-trifluoromethyl-benzene (5.43 g, 20.1 nunol) was dissolved in 10 mL anhydrous DMSO. Sodium methoxide (5.85 mL of a 25% w/w solution in methanol) was added by syringe. The yellow solution immediately turned pink-orange, with heat evolved. The reaction was left stirring overnight at room temperature, then EtOAc (300 mL) was added and the mixture was washed once with dilute HCl aqueous solution, thrice with water and once with brine. The organic solution was dried (Na$_2$SO$_4$), filtered and concentrated in vacuo. The residue was purified through a short plug of silica gel and 4.65 g of 2-methoxy-1,3-dinitro-5-trifluoromethylbenzene was isolated as a yellow solid.

2-Methoxy-1,3-dinitro-5-trifluoromethylbenzene (3.0 g, 11.3 mmol) was dissolved in 100 mL 50:50 EtOAc: MeOH. Ammonium formate (7.06 g, 112 inmol) was added followed by palladium-on-carbon catalyst (1.0 g). The reaction was heated to a gentle reflux for 45 min, then allowed to cool, and filtered through a plug of diatomaceous earth. The calalyst was washed with EtOAc repeatedly, and the filtrate was in vacuo. The residue was taken up in 500 ml 50% EtOAc in hexanes and filtered through a short plug of silica gel. The filtrate was concentrated in vacuo, providing 2.15 g (10.4 mmol, 95%) of 2-methoxy-5-trifluoromethyl-benzene-1,3-diamine as a brown oil.

2-Methoxy-5-trifluoromethylbenzene-1,3-diamine (2.32 g, 11.3 mmol) was dissolved in 50 mL anhydrous dichloromethane. The solution was cooled to 0° C., and pyridine (3.64 mL, 45.0 mmol) and methane sulfonyl chloride (0.89 mL, 11.5 mmol) were added. The reaction was left to stir overnight at room temperature. A few more drops (0.1 mL) of methane sulfonyl chloride were added and the reaction stirred an extra day. Then 200 mL EtOAc, was added and the solution washed once with 100 mL water, twice with 15 mL saturated aqueous $NH_4Cl$ solution and finally with brine. The organic solution was dried ($MgSO_4$), filtered and concentrated in vacuo. The residue was purified by column chromatography on silica gel using EtOAc/hexanes eluent mixtures, providing N-(3-amino-2-methoxy-5-trifluoromethyl-phenyl)-methanesulfonamide (1870 mg, 6.58 mmol, 58% yield) as an orange solid.

N-(3-Amino-2-methoxy-5-trifluoromethyl-phenyl)-methanesulfonamide (86 mg, 0.30 mmol) was dissolved in 20 mL dichloromethane. 10 mL Saturated aqueous $NaHCO_3$ solution was added, the mixture was cooled to 0° C. and, while not stirring, the mixture was treated with phosgene (0.6 mL of a 2 M solution in toluene, 1.2 mmol) by addition to the organic layer via syringe in one portion. The mixture was then stirred vigorously for 25 min, then the layers were separated. The aqueous layer was extracted once with dichloromethane and the combined organics were dried ($MgSO_4$), filtered and the dichloromethane was removed in vacuo. To the isocyanate residue was then added the 4-(2, 6-dimethyl-pyrimidin-4-yloxy)-naphthalen-1-ylamine (see Example 3) in 6 mL anhydrous THF. The reaction mixture was left stirring at room temperature for 12 days, then the solvent was removed in vacuo. The resulting reddish solid was purified by column chromatography on silica gel using dichloromethane/MeOH eluent mixtures. The resulting white foam was triturated with hot acetonitrile to yield the title compound as white powder (69 mg), mp: 212-213° C.

Example 9

Synthesis of 1-(2-methoxy-5-trifluoromethyl-phenyl)-3-{4-[6-methyl-2-(2-morpholin-4-yl-ethyl)-pyrimidin-4-yloxy]-naphthalen-1-yl}-urea

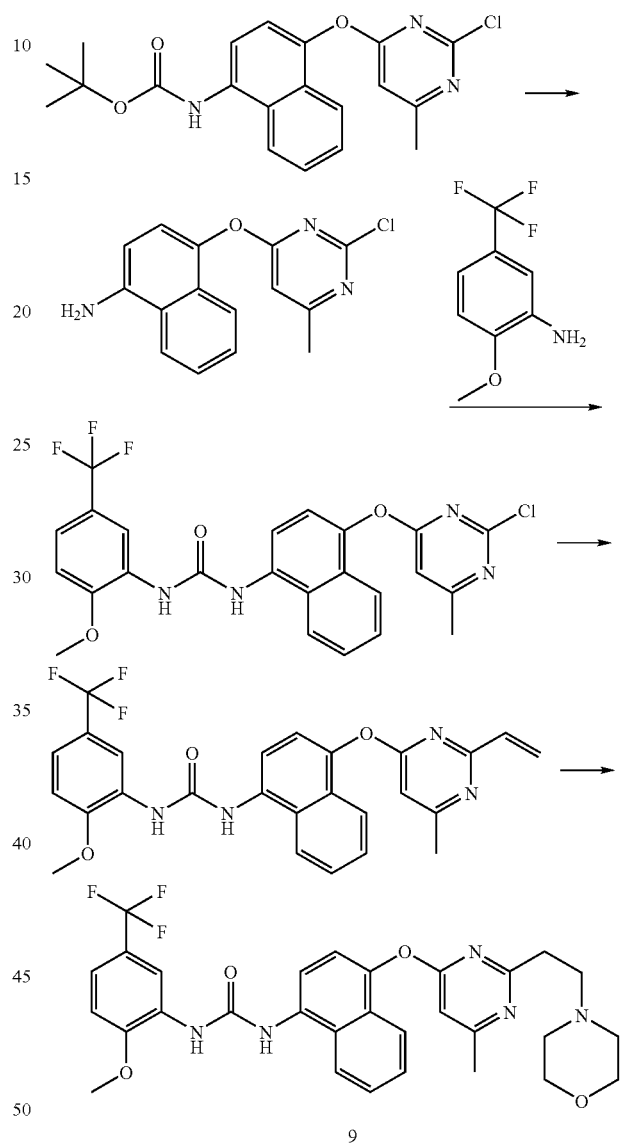

9

To a solution of (4-Boc-amino-naphthyl)-(2-chloro-6-methyl-pyrimidinyl)-ether (see Example 1) (10.0 g, 25.9 rnmol) in dichloromethane (100 mL) was added an excess of trifluoroacetic acid (92 mL). The reaction was stirred at room temperature for 2.5 h, then concentrated in vacuo. The residue was taken up in EtOAc and washed with saturated $NaHCO_3$ solution (2×), water (2×), and brine. The organic extract was then dried over $MgSO_4$ and concentrated to give the product as a solid (7.4 g, quantitative yield) which was carried forward without further purification.

To a solution of 2-methoxy-5-trifluoromethylaniline (5.49 g, 28.7 mmol) in toluene (275 mL) was added diphosgene (2.84 g, 14.4 mmol) in one portion. The reaction was refluxed for 3.5 h, then cooled, and concentrated in vacuo.

The residue was taken up in THF (25 mL) and the resulting solution was added dropwise to a solution of the naphthylamine (7.46 g, 26.1 mmol) in THF (250 mL) kept at 0° C. The reaction was allowed to warm to room temperature and stirred for 16 h, followed by concentration in vacuo. The resulting solid was triturated with EtOAc to give the desired urea intermediate (7.5 g, 57%) as a colorless solid which was used without further purification.

The above urea (4.0 g, 8.0 mmol) was suspended in a mixture of toluene (40 mL) and 1,4-dioxane (40 mL) under an atmosphere of $N_2$. $Pd(PPh_3)_4$ (750 mg, 0.673 mmol), BHT (100 mg), and (vinyl)tributyltin (4.0 mL, 13 mmol) were added, and the mixture heated to 120° C. for 12 h. The mixture was cooled, diluted with dichloromethane (100 mL), washed with saturated $NaHCO_3$ solution (20 mL), dried over $MgSO_4$, and concentrated in vacuo. The residue was triturated with $Et_2O$ to give the desired 2-vinylpyrimidine intermediate as a tan powder (1.55 g, 3.14 mmol) which was used without further purification.

A solution of the above 2-vinylpyrimidine intermediate (76 mg, 0.15 mmol), morpholine (25 μL, 0.29 mmol), and acetic acid (15 μL, 0.26 mmol) in EtOH (3 mL) was heated to 80° C. in a sealed tube for 22 h. The solvent was removed and the residue taken up in dichloromethane (100 mL), washed with saturated $NaHCO_3$ solution (15 mL), dried over $MgSO_4$, and concentrated. Purification by silica gel chromatography (0 to 100% EtOAc in hexanes, then 0 to 10% MeOH in dichloromethane; gradient elution) provided the title compound as a red glass (45 mg, 50%).

Assessment of Biological Properties

Pharmacokinetic properties of p38 inhibitor compounds can be measured by known methods. hihibition of p38 MAP kinase and inhibition of cytokine production are measured as follows:

Inhibition of P38 MAP Kinase

To determine binding affinities for compounds to p38 MAP kinase, a fluorescence binding assay is used as described [Pargellis, C., Tong, L., Churchill, L., Cirillo, P. F., Gilmore, T., Graham, A. G., Grob, P. M., Hickey, E. R., Moss, N., Pav, S. & Regan, J. Inhibition of p38 MAP kinase by utilizing a novel allosteric binding site. *Nature Structural Biology* 9, 268-272 (2002)]. Binding studies are conducted in aqueous solutions prepared using binding buffer: 20 mM Bis-TRIS Propane (pH 7.0), 2 mM EDTA, 0.01% $NaN_3$, and 0.15% n-octylglucoside. Kinetic data for the association of SK&F 86002 to p38 MAP kinase is collected on a Kintech fluorescence detector system equipped with a stopped flow controller. The data is fit simultaneously to an appropriate equation describing kinetic binding for a simple 1-step binding mechanism [Morelock, M. M., Pargellis, C. A., Graham, E. T., Lamarre, D. & Jung, G. Time-resolved ligand exchange reactions: kinetic models for competitive inhibitors with recombinant human renin. *J. Med. Chem.* 38, 1751-1761 (1995)]. The exchange curve assays are run as two half reactions using an SLM Aminco Bowman Series 2 Model SQ-340 fluorescence detector. Preliminary equilibrium are set up with two half reactions differing in the order of addition of the two p38 MAP kinase inhibitors. In the first half reaction, p38 MAP kinase and SK&F 86002 are preincubated for 3 minutes. In the second half reaction p38 MAP kinase is preincubated with BIRB 796 for 60 minutes. A net dissociation of the fluorescent probe, SK&F 86002, is observed for the first half reaction and a net association is observed for the second half reaction. The raw data from both half reactions are fitted simultaneously to an equation describing simple competitive inhibition[Morelock, M. M., Pargellis, C. A., Graham, E. T., Lamarre, D. & Jung, G. Time-resolved ligand exchange reactions: kinetic models for competitive inhibitors with recombinant human renin. *J. Med. Chem.* 38, 1751-1761 (1995)]. BIRB 796 (chemical name: 1-(5-tert-butyl-2-p-tolyl-2H-pyrazol-3-yl)-3-[4-(2-morpholin-4-yl-ethoxy)-naphthalen-1-yl]-urea) was synthesized as described [Cirillo, P., Gilmore, T. A., Hickey, E., Regan, J. & Zhang, L. H. Aromatic heterocyclic compounds as antiinflammatory agents. (WO0043384) Dec. 9, 1999].

Preferred compounds were evaluated and had $IC_{50}$<1 μM in this assay, confirming inhibition of p38 MAP Kinase.

The compounds of the invention possess selectivity for p38 MAP Kinase over one or more kinases. These kinases include Src family of kinases, especially Lyn.

Inhibition of TNF Production in THP Cells

The inhibition of cytokine production can be observed by measuring inhibition of TNFα in lipopolysaccharide stimulated THP cells (for example, see W. Prichett et al., 1995, *J. Inflammation*, 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was nonsterile. Initial stock solutions were made in DMSO followed by dilution into RPMI 1640 2-fold higher than the desired final assay concentration. Confluent THP.1 cells ($2 \times 10^6$ cells/ml, final conc.; American Type Culture Company, Rockville, Md.) were added to 96 well polypropylene round bottomed culture plates (Costar 3790; sterile) containing 125 μl test compound (2 fold concentrated) or DMSO vehicle (controls, blanks). DMSO concentration did not exceed 0.2% final. Cell mixture was allowed to preincubate for 30 min, 37° C., 5% $CO_2$ prior to stimulation with lipopolysaccharide (LPS; 1 μg/ml final; Siga L-2630, from E.coli serotype 0111.B4; stored as 1 mg/ml stock in endotoxin screened distilled $H_2O$ at −80° C.). Blanks (unstimulated) received $H_2O$ vehicle; final incubation volume was 250 μl. Overnight incubation (18-24 hr) proceeded as described above. Assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated $IC_{50}$ value is the concentration of the test compound that caused a 50% decrease in the maximal TNFα production.

Preferred compounds have an $IC_{50}$<1 μM in this assay.

Inhibition of Other Cytokines

By similar methods using peripheral blood monocytic cells, appropriate stimuli, and commercially available ELISA kits (or other method of detection such as radioimmunoassay), for a particular cytokine, inhibition of IL-1beta, GM-CSF, IL-6 and IL-8 can be demonstrated for preferred compounds (for example, see J. C. Lee et al., 1988, *Int. J. Immunopharmacol.*, 10, 835).

What is claimed is:

1. A compound of the formula (I):

(I)

[Chemical structure diagram showing formula I with R1, R2, R3 substituents on phenyl ring, urea linker, naphthalene, and pyrimidine with W, X, and CH3]

wherein

R$_1$ is —CF$_3$, —CH(CH$_3$)(CF$_3$), —CH(CF$_3$)$_2$, —OCF$_3$, —CF$_2$CF$_3$;

R$_2$ is C1-5 alkyl;

R$_3$ is attached at the 3- or 4-position on the phenyl ring and is hydrogen, —NH$_2$ or R$_4$—S(O)$_2$—NH— wherein R$_4$ is chosen from C$_{1-5}$ alkyl or carbocycle;

W is CH or an N atom;

X is chosen from

C1-5 alkyl or C1-5 alkoxy each substituted by morpholinyl, piperazinyl, pyrrolidinyl, triazolyl, imidazolyl or piperadinyl each ring being further optionally substituted with C1-3 alkyl;

or X is —NHR$^a$ wherein R$^a$ is heterocyclyl C1-3 alkyl wherein the heterocycyl is chosen from tetrahydrofuran, pyrrolidinyl and morpholinyl, each optionally substituted by one to two C1-5 alkyl, C1-5 alkoxy, hydroxy, halogen or amino optionally mono- or di-substituted by C1-3 alkyl;

or the pharmaceutically acceptable acids, esters, salts or isomers thereof.

2. The compound according to claim 1 wherein:

R$_1$ is —CF$_3$, —CH(CH$_3$)(CF$_3$), —CH(CF$_3$)$_2$, —OCF$_3$ or —CF$_2$CF$_3$;

R$_2$ is C$_{1-3}$ alkyl;

W is an N atom;

X is chosen from

C1-5 alkyl or C1-5 alkoxy each substituted by morpholinyl, piperazinyl, pyrrolidinyl, triazolyl, imidazolyl or piperadinyl each ring being further optionally substituted with C1-3 alkyl;

or X is —NHR$^a$ wherein R$^a$ is heterocyclyl C1-3 alkyl wherein the heterocycyl is chosen from tetrahydrofuran, pyrrolidinyl and morpholinyl, each is optionally substituted by one to two C1-3 alkyl, C1-3 alkoxy, hydroxy, halogen or amino optionally mono- or di-substituted by C1-2 alkyl.

3. The compound according to claim 2 wherein:

R$_1$ is —CF$_3$, —CH(CH$_3$)(CF$_3$), —CH(CF$_3$)$_2$ or —CF$_2$CF$_3$;

R$_2$ is C$_{1-2}$ alkyl.

4. The compound according to claim 3 wherein:

R$_1$ is —CF$_3$;

R$_2$ is —CH$_3$.

5. The compound according to claim 4 wherein:

X is chosen from

—CH$_2$CH$_2$—N(piperazinyl)—CH$_3$,

—CH$_2$CH$_2$—N(piperidinyl),

—CH$_2$CH$_2$—N(morpholinyl), —CH$_2$—N(morpholinyl),

—NHCH$_2$(tetrahydrofuranyl), —NHCH$_2$CH$_2$(pyrrolidinyl),

—CH$_2$CH$_2$(pyrrolidinyl) and

—NHCH$_2$CH$_2$—N(morpholinyl).

6. The compound according to claim 5 wherein:

X is chosen from

—CH$_2$—N(morpholinyl), —NHCH$_2$(tetrahydrofuranyl),

—NHCH$_2$CH$_2$(pyrrolidinyl) and

—NHCH$_2$CH$_2$—N(morpholinyl).

7. A compound chosen from:

1-(2-Methoxy-5-trifluoromethyl-phenyl)-3-[4-(6-methyl-2-morpholin-4-ylmethyl-pyrimidin-4-yloxy)-naphthalen-1-yl]-urea;

1-(2-Methoxy-5-trifluoromethyl-phenyl)-3-(4-{6-methyl-2-[(tetrahydro-furan-2-ylmethyl)-amino]-pyrimidin-4-yloxy}-naphthalen-1-yl)-urea;

1-(2-Methoxy-5-trifluoromethyl-phenyl)-3-{4-[6-methyl-2-(2-pyrrolidin-1-yl-ethylamino)-pyrimidin-4-yloxy]-naphthalen-1-yl}-urea and 1-(2-Methoxy-5-trifluoromethyl-phenyl)-3-{4-[6-methyl-2-(2-morpholin-4-yl-ethylamino)-pyrimidin-4-yloxy]-naphthalen-1-yl}-urea or the pharmaceutically acceptable acids, esters, salts or isomers thereof.

8. A compound chosen from:

1-(2-Methoxy-5-trifluoromethoxy-phenyl)-3-{4-[6-methyl-2-(2-pyrrolidin-1-yl-ethylamino)-pyrimidin-4-yloxy]-naphthalen-1-yl}-urea;

-continued 1-(2-Methoxy-5-trifluoromethoxy-phenyl)-3-[4-(6-methyl-2-morpholin-4-ylmethyl-pyrimidin-4-yloxy)-naphthalen-1-yl]-urea;
1-(2-Methoxy-5-trifluoromethoxy-phenyl)-3-{4-[6-methyl-2-(4-methyl-piperazin-1-ylmethyl)-pyrimidin-4-yloxy]-naphthalen-1-yl}-urea;
1-(2-Methoxy-5-trifluoromethoxy-phenyl)-3-[4-(6-methyl-2-pyrrolidin-1-ylmethyl-pyrimidin-4-yloxy)-naphthalen-1-yl]-urea;
1-{4-[2-(2-Imidazol-1-yl-ethoxy)-6-methyl-pyrimidin-4-yloxy]-naphthalen-1-yl}-3-(2-methoxy-5-trifluoromethoxy-phenyl)-urea;
1-[2-Methoxy-5-(2,2,2-trifluoro-ethyl)-phenyl]-3-{4-[6-methyl-2-(1-methyl-piperidin-4-ylmethoxy)-pyrimidin-4-yloxy]-naphthalen-1-yl}-urea;
1-[2-Methoxy-5-(2,2,2-trifluoro-ethyl)-phenyl]-3-{4-[6-methyl-2-(3-morpholin-4-yl-propylamino)-pyrimidin-4-yloxy]-naphthalen-1-yl}-urea;
1-(2-Methoxy-5-trifluoromethoxy-phenyl)-3-{4-[6-methyl-2-(3-morpholin-4-yl-propylamino)-pyrimidin-4-yloxy]-naphthalen-1-yl}-urea;
1-[2-Methoxy-5-(2,2,2-trifluoro-1-trifluoromethyl-ethyl)-phenyl]-3-[4-(6-methyl-2-morpholin-4-ylmethyl-pyrimidin-4-yloxy)-naphthalen-1-yl]-urea and
1-(2-Methoxy-5-trifluoromethyl-phenyl)-3-{4-[6-methyl-2-(4-methyl-piperazin-1-ylmethyl)-pyrimidin-4-yloxy]-naphthalen-1-yl}-urea or the pharmaceutically acceptable acids, esters, salts or isomers thereof.

9. A compound chosen from 1-(2-Methoxy-5-trifluoromethyl-phenyl)-3-[4-(6-methyl-2-morpholin-4-ylmethyl-pyrimidin-4-yloxy)-naphthalen-1-yl]-urea;
1-(2-Methoxy-5-trifluoromethyl-phenyl)-3-{4-[6-methyl-2-(2-pyrrolidin-1-yl-ethylamino)-pyrimidin-4-yloxy]naphthalen-1-yl}-urea;
and
1-(2-Methoxy-5-trifluoromethyl-phenyl)-3-{4-[6-methyl-2-(2-morpholin-4-yl-ethylamino)-pyrimidin-4-yloxy]-naphthalen-1-yl}-urea or the pharmaceutically acceptable acids, esters, salts or isomers thereof.

10. A pharmaceutical composition containing a pharmaceutically effective amount of a compound according to claim 1 and one or more pharmaceutically acceptable carriers and/or adjuvants.

* * * * *